(12) United States Patent
Goldfine et al.

(10) Patent No.: US 7,518,360 B2
(45) Date of Patent: Apr. 14, 2009

(54) HYBRID WOUND/ETCHED WINDING CONSTRUCTS FOR SCANNING AND MONITORING

(75) Inventors: Neil J. Goldfine, Newton, MA (US);
Darrell E. Schlicker, Watertown, MA (US); Andrew P. Washabaugh, Chula Vista, CA (US); Ian C. Shay, Cambridge, MA (US); Mark D. Windoloski, Burlington, MA (US); Christopher Root, Somerville, MA (US); Vladimir A. Zilberstein, Chestnut Hill, MA (US); David C. Grundy, Reading, MA (US); Vladimir Tsukernik, West Roxbury, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 131 days.

(21) Appl. No.: 11/809,555

(22) Filed: Jun. 1, 2007

(65) Prior Publication Data
US 2008/0258720 A1 Oct. 23, 2008

Related U.S. Application Data

(62) Division of application No. 10/853,009, filed on May 24, 2004, now abandoned.

(60) Provisional application No. 60/473,180, filed on May 23, 2003.

(51) Int. Cl.
*G01N 27/82* (2006.01)
*G01R 33/12* (2006.01)

(52) U.S. Cl. ............... 324/240; 324/242; 324/234; 324/238

(58) Field of Classification Search .......... 324/209, 324/227, 228, 232, 239, 240, 241, 242, 243, 324/252
See application file for complete search history.

(56) References Cited

U.S. PATENT DOCUMENTS

| | | | |
|---|---|---|---|
| 3,449,664 A | * | 6/1969 | Smith .................... 324/235 |
| 3,665,756 A | | 5/1972 | Russell |
| 3,977,236 A | | 8/1976 | Raatz et al. |
| 4,095,181 A | * | 6/1978 | Harris et al. .............. 324/238 |

(Continued)

OTHER PUBLICATIONS

Bowler, N., "Theory of Four-Point Direct-Current Potential Drop Measurements on a Metal Plate" Research in Nondestructive Evaluation, vol. 17, pp. 29-48, (2006).*

(Continued)

*Primary Examiner*—Kenneth J Whittington
(74) *Attorney, Agent, or Firm*—Hamilton, Brook, Smith & Reynolds, P.C.

(57) ABSTRACT

Combined wound and micro-fabricated winding constructs are described for the inspection of materials and the detection and characterization of hidden features or flaws. These constructs can be configured as sensors or sensor arrays that are surface mounted or scanned over conducting and/or magnetizable test materials. The well-defined geometry obtained micro-fabricated windings and from carefully wound coils with known winding positions permits the use of model based inversions of sensed responses into material properties. In a preferred embodiment, the primary winding is a wound coil and the sense elements are etched or printed. The drive or sense windings can also be mounted under fasteners to improve sensitivity to hidden flaws. Ferrites and other means may be used to guide the magnetic flux and enhance the magnetic field in the test material.

30 Claims, 16 Drawing Sheets

U.S. PATENT DOCUMENTS

| | | | |
|---|---|---|---|
| 4,142,154 | A | 2/1979 | Couchman |
| 4,203,069 | A | 5/1980 | Davis |
| 4,247,819 | A | 1/1981 | Shimada et al. |
| 4,271,393 | A * | 6/1981 | Hansen et al. ............... 324/240 |
| 4,383,218 | A | 5/1983 | Hansen |
| 4,454,790 | A | 6/1984 | Rieben |
| 4,528,856 | A | 7/1985 | Junker |
| 4,706,020 | A | 11/1987 | Viertl et al. |
| 4,814,690 | A | 3/1989 | Melcher et al. |
| 4,823,606 | A | 4/1989 | Malicki |
| 4,846,001 | A | 7/1989 | Kibblewhite |
| 5,015,951 | A | 5/1991 | Melcher |
| 5,023,549 | A | 6/1991 | Dau et al. |
| 5,047,719 | A | 9/1991 | Johnson et al. |
| 5,156,636 | A | 10/1992 | Kuljis |
| 5,291,789 | A | 3/1994 | Walton |
| 5,399,968 | A * | 3/1995 | Sheppard et al. ............ 324/242 |
| 5,453,689 | A | 9/1995 | Goldfine et al. |
| 5,499,540 | A | 3/1996 | Whaley et al. |
| 5,510,709 | A * | 4/1996 | Hurley et al. ............... 324/242 |
| 5,549,803 | A | 8/1996 | Schoess et al. |
| 5,610,515 | A | 3/1997 | Soules |
| 5,648,721 | A | 7/1997 | Wincheski et al. |
| 5,675,087 | A | 10/1997 | MacLauchlan |
| 5,739,686 | A | 4/1998 | Naughton et al. |
| 5,793,206 | A | 8/1998 | Goldfine et al. |
| RE36,986 | E | 12/2000 | Melcher |
| 6,188,218 | B1 | 2/2001 | Goldfine et al. |
| 6,271,664 | B1 * | 8/2001 | Logue ........................ 324/240 |
| 6,380,747 | B1 | 4/2002 | Goldfine et al. |
| 6,479,989 | B2 | 11/2002 | Taylor |
| 6,486,673 | B1 | 11/2002 | Goldfine et al. |
| 6,545,469 | B1 * | 4/2003 | Batzinger et al. ........... 324/238 |
| 6,657,429 | B1 | 12/2003 | Goldfine et al. |
| 6,727,690 | B2 | 4/2004 | Soules |
| 6,727,691 | B2 | 4/2004 | Goldfine et al. |
| 6,781,387 | B2 | 8/2004 | Goldfine et al. |
| 6,784,662 | B2 | 8/2004 | Schlicker et al. |
| 6,888,346 | B2 | 5/2005 | Wincheski et al. |
| 6,952,095 | B1 | 10/2005 | Goldfine et al. |
| 6,992,482 | B2 | 1/2006 | Shay et al. |
| 2001/0054896 | A1 | 12/2001 | Mednikov et al. |
| 2002/0075006 | A1 | 6/2002 | Goldfine et al. |
| 2002/0163333 | A1 | 11/2002 | Schlicker et al. |
| 2003/0071614 | A1 | 4/2003 | Buttle |
| 2003/0071615 | A1 | 4/2003 | Schlicker et al. |
| 2003/0173958 | A1 | 9/2003 | Goldfine et al. |
| 2004/0100277 | A1 | 5/2004 | Tam |
| 2004/0124833 | A1 | 7/2004 | Kliman et al. |
| 2005/0007106 | A1 | 1/2005 | Goldfine et al. |
| 2005/0083032 | A1 | 4/2005 | Goldfine et al. |
| 2007/0007955 | A1 | 1/2007 | Goldfine et al. |

OTHER PUBLICATIONS

Navy Phase I Proposal, titled "In-situ projected field and near surface sensors for direct condition monitoring of engine hot section, components" Topic #N06-T01 I, dated Apr. 13, 2006.*
Auld, B.A. and Moulder, J.C. (1999), "Review of Advances in Quantitative Eddy-Current Nondestructive Evaluation," Journal of Nondestructive Evaluagion, vol. 18, No. 1.*
Bozorth, R.M., Ferromagnetism, IEEE Press, 197g.*
Bray, D.E., ed., Residual Stress Measurement and General Nondestructive Evaluation, PVP-vol. 429, ASME Pressure Vessels and Piping Conference, Atlanla, GA, ASME, 2001.*
Hydrogen in Metals, Proceedings of the Second Japan Institute of Metals, International Symposium, 1979.*
Interrante, C. and Pressouyre, G. "Current Solutions to Hydrogen Problems in Steels," Proceedings of the First International Conference, ASM, 1982.*
Lawrence, S.C. "Hydrogen Detection Gage," Hydrogen Embrittlement Testing, ASTM STP 543, 1974, pp. 83-105.*
Navy Phase I Proposal, titled "Wireless Communications with Electromagnetic Sensor Networks for Nondestructive Evauation," Topic #N01-174, dated Aug. 13, 2001.*
Air Force Phase I Proposal, titled "Three Dimensional Magnetic imaging of Damage in Multiple Layer Aircraft Structures" Topic #AF02-281, dated Jan. 14, 2002.*
DOE Phase 11 Proposal, titled "Intelligent Probes for Enhanced Non-Destructive Determination of Degradation m Hot-Gas-Path Components," Topic #44c, dated Mar. 23, 2002.*
Air Force Phase II Proposal, titled "Detraction and Imaging of Damuge, Including Hydrogen Embrittlement Effects in landing Gear and Other High-Strength Steel Components." Topic #AF0I-308, dated Apr. 9, 2002.*
Strategic Environmental Research and Development Program Proposal, titled "High Resolution Inductive Sensor Arrays for UXO Delection, Identification and Clutter Suppression,", SON #UXSON-02-03, dated Apr. 17, 2002.*
NASA Phase II Proposal, titled "Shaped Field Giant Magnetoresisitive Sensor Arrays for Materials Testing" Topic #O1-II A1.05-8767, dated May 2, 2002.*
Navy Phase I Proposal, titled "Observability Enhancement and Uncertainty Mitigation for Engine Rotating Component PHM." Topic #N02-188, dated Aug. 14, 2002.*
NASA Phase I Proposal, titled "Non-Destructive Evaluation, Health Moniloring and Life Determination of Aerospace Vehicles/Systems" Topic #02-H5.03-8767, dated Aug. 21, 2002.*
Final Report submitted to FAA, titled "Crack Detection Capability Comparison of JENTEK MWM-Array and GE Eddy-current Sensors on Titanium ENSIP Plates" dated Sep. 28, 2001. Contract #DTFA03-00-C-00026, option 2 CLIN006 and 006a.*
Final Report submitted to FAA, titled "Aircraft Hidden Damage Detection and Assessment with Conformable Eddy Current Arrays," FAA Contract DTFA03-O 1-C-00024, dared Mar. 29, 2002.*
Final Report submitted ro NASA, titled "Shaped Field Giant Magnetoresisitive Sensor Arrays for Materials Testing" dated May 3, 2002.*
Final Report submitted to Air Force, titled "Detection and Imaging of Damage, Including Hydrogen Embrittlement Effects in Landing Gear and Other High-Strength Steel Components" dated Jul. 3, 2002.*
Final Proposal submiffed to Navy, titled "Wireless Communications with Electromagnetic Sensor Networks for Nondestructive Evaluation" dated Jul. 15, 2002.*
Final Report titled "Portable Accumulated Fatigue Damage Inspection System Using Permanently Mourned and Wide-Area Imaging MWM-Arrays," dated Aug. 23, 2002.*
Technical paper titled "MWM Eddy-Current Arrays for Crack Initiation and Growth Monitoring" submitted to International Journal of Fatigue, from the International Conference on Fatigue Damage of Structural Materials IV, Hyannis, MA, 2002.*
Technical paper titled "Conformable Eddy-Current Sensors and Arrays for Fleetwide Gas Turbine Component Quality Assessment" published in ASME Journal of Engineering for Gas Turbines and Power, vol. 124, No. 4, pp. 904-909; Oct. 2002.*
Technical paper titled "Residual and Applied Stress Estimation from Directional Magnetic Permeability Measurements with MWM Sensors" published in ASME Journal of Pressure Vessel Technology, vol. 124, pp. 375-381, Aug. 2002.*
Technical paper titled "Fatigue and Stress Monitoring Using Scanning and Permanently Mounted MWM-Arrays" presented at 29th Annual Review of Progress in QNDE; Bellingham, Washington, Jul. 2002.*
Technical paper titled "Absolute Electrical Property, Imaging using High Resolution Inductive, Magnetoresistive and Capacitive Sensor Arrays for Materials Characterization" presented at 11th International Symposium on Nondestructive Characterization of Materials, Berlin, Germany, Jun. 2002.*
Technical paper titled "Application of MWM® Eddy-Current Technology during Production of Coated Gas Turbine Components" presented at 11th International Symposium on Nondestructive Characterization of Materials, Berlin, Germany, Jun. 2002.*

Technical paper titled "Friction Stir Weld Inspection through Conductivity Imaging using Shaped Field MWM-Arrays" presented at ASM Trends in Welding Conference, Callaway Gardens, GA, Apr. 2002.*

Technical paper and presentation slides, titled "MWM-Array Characterization and Imaging of Combustion Turbine Components," presented at EPRI International Conference on Advances in Life Assessment and Optimization of Fossil Power Plants, Orlando, FL, Mar. 2002.*

Technical paper titled "Surface Mounted and Scanning Periodic Field Eddy-Current Sensors for Structural Health Monitoring" presented at the IEEE Aerospace Conference, Mar. 2002.*

Presentation slides titled "Corrosion Detection and Prioritzation Using Scanning and Permanently Mountable MWM Eddy-Current Arrays" U.S. Army Corrosion Summit, Mar. 2002.*

Technical paper and presentation slides titled "Shapod-Field Eddy-current Sensors and Arrays" SPIE 7th Annual International Symposium: NDE for Health Monitoring and Diagonostics, Mar. 2002.*

Technical paper titled "Corrosion Detection and Prioritization Using Scanning and Permanently Mounted MWM Eddy-Current Arrays" Tri-Service Corrosion Conference, Jan. 2002.*

Technical presentation slides "Condition Assessment of Engine Component Materials Using MWM Eddy-Current Sensors" ASNT Fall Conference, Columbus, OH, Oct. 2001.*

Technical paper titled "Flexible Eddy Current Sensors and Scanning Arrays for Inspection of Steel and Alloy Components," 7th EPRI Steam Turbine/Generator Workshop and Vendor Exposition, Baltimore, MD, Aug. 2001.*

Technical paper titled "Applications for Conformable Eddy Current Sensors including High Resolution and Deep Penetration Sensor Arrays in Manufacturing and Power Generation," ASME 7th NDE Topical Conference, San Antonio, Texas, 2001.*

Auld, B.A. and Moulder, J.C. (1999), "Review of Advances in Quantitative Eddy-Current Nondestructive Evaluation," Journal of Nondestructive Evaluation, vol. 18, No. 1.

Air Force Phase II Proposal, titled "Three Dimensional Magnetic Imaging of Damage in Multiple Layer Aircraft Structures," Topic #AF02-281, dated Feb. 20, 2003.

Technical paper titled "*MWM Eddy Current Sensor Array Imaging of Surface and Hidden Corrosion for Improved Fleet Readiness and Cost Avoidance,*" presented at U.S. Army Corrosion Conference, Clearwater Beach; FL, Feb. 11-13, 2003.

Technical paper titled "*MWM Eddy Current Sensor Array Characterization of Aging Structures Including Hidden Damage Imaging,*" presented to the Aerospace Committee, NACE Conference, San Diego; CA, Mar. 17-19, 2003.

Bowler, N., "Theory of Four-Point Direct-Current Potential Drop Measurements on a Metal Plate," Research in Nondestructive Evaluation, vol. 17, pp. 29-48, (2006).

Navy Phase I Proposal, titled "In-situ projected field and near surface sensors for direct condition monitoring of engine hot section, components," Topic #N06-T011, dated Apr. 13, 2006.

Auld, B.A. and Moulder, J.C. (1999), "Review of Advances in Quantitative Eddy-Current Nondestructive Evaluation," Journal of Nondestructive Evaluation, vol. 18, No. 1.

Bozorth, R.M., Ferromagnetism, IEEE Press, 1978.

Bray, D.E., ed., Residual Stress Measurement and General Nondestructive Evaluation, PVP-vol. 429, ASME Pressure Vessels and Piping Conference, Atlanta, GA, ASME, 2001.

Hydrogen in Metals, Proceedings of the Second Japan Institute of Metals, International Symposium, 1979.

Interrante, C. and Pressouyre, G. "Current Solutions to Hydrogen Problems in Steels," Proceedings of the First International Conference, ASM, 1982.

Lawrence, S.C. "Hydrogen Detection Gage," Hydrogen Embrittlement Testing, ASTM STP 543, 1974, pp. 83-105.

Navy Phase I Proposal, titled "Wireless Communications with Electromagnetic Sensor Networks for Nondestructive Evaluation," Topic #N01-174, dated Aug. 13, 2001.

Air Force Phase I Proposal, titled "Three-Dimensional Magnetic Imaging of Damage in Multiple Layer Aircraft Structures," Topic #AF02-281, dated Jan. 14, 2002.

DOE Phase II Proposal, titled "Intelligent Probes for Enhanced Non-Destructive Determination of Degradation in Hot-Gas-Path Components," Topic #44c, dated Mar. 23, 2002.

Air Force Phase II Proposal, titled "Detection and Imaging of Damage, Including Hydrogen Embrittlement Effects in Landing Gear and Other High-Strength Steel Components," Topic #AF01-308, dated Apr. 9, 2002.

Strategic Environmental Research and Development Program Proposal, titled "High Resolution Inductive Sensor Arrays for UXO Detection, Identification and Clutter Suppression,", SON #UXSON-02-03, dated Apr. 17, 2002.

NASA Phase II Proposal, titled "Shaped Field Giant Magnetoresistive Sensor Arrays for Materials Testing," Topic #01-II A1.05-8767, dated May 2, 2002.

Navy Phase I Proposal, titled "Observability Enhancement and Uncertainty Mitigation for Engine Rotating Component PHM," Topic #N02-188, dated Aug. 14, 2002.

NASA Phase I Proposal, titled "Non-Destructive Evaluation, Health Monitoring and Life Determination of Aerospace Vehicles/Systems," Topic #02-H5.03-8767, dated Aug. 21, 2002.

Final Report submitted to FAA, titled "Crack Detection Capability Comparison of JENTEK MWM-Array and GE Eddy-current Sensors on Titanium ENSIP Plates", dated Sep. 28, 2001, Contract #DTFA03-00-C-00026, option 2 CLIN006 and 006a.

Final Report submitted to FAA, titled "Aircraft Hidden Damage Detection and Assessment with Conformable Eddy Current Arrays,"FAA Contract DTFA03-01-C-00024, dated Mar. 29, 2002.

Final Report submitted to NASA, titled "Shaped Field Giant Magnetoresistive Sensor Arrays for Materials Testing," dated May 3, 2002.

Final Report submitted to Air Force, titled "Detection and Imaging of Damage, Including Hydrogen Embrittlement Effects in Landing Gear and Other High-Strength Steel Components," dated Jul. 3, 2002.

Final Report submitted to Navy, titled "Wireless Communications with Electromagnetic Sensor Networks for Nondestructive Evaluation,"dated Jul. 15, 2002.

Final Report titled "Portable Accumulated Fatigue Damage Inspection System Using Permanently Mounted and Wide-Area Imaging MWM-Arrays," dated Aug. 23, 2002.

Technical paper titled "MWM Eddy-Current Arrays for Crack Initiation and Growth Monitoring," submitted to International Journal of Fatigue, from the International Conference on Fatigue Damage of Structural Materials IV, Hyannis, MA, 2002.

Technical paper titled "Conformable Eddy-Current Sensors and Arrays for Fleetwide Gas Turbine Component Quality Assessment," published in ASME Journal of Engineering for Gas Turbines and Power, vol. 124, No. 4, pp. 904-909; Oct. 2002.

Technical paper titled "Residual and Applied Stress Estimation from Directional Magnetic Permeability Measurements with MWM Sensors," published in ASME Journal of Pressure Vessel Technology, vol. 124, pp. 375-381; Aug. 2002.

Technical paper titled "Fatigue and Stress Monitoring Using Scanning and Permanently Mounted MWM-Arrays," presented at 29th Annual Review of Progress in QNDE; Bellingham, Washington; Jul. 2002.

Technical paper titled "Absolute Electrical Property Imaging using High Resolution Inductive, Magnetoresistive and Capacitive Sensor Arrays for Materials Characterization," presented at 11th International Symposium on Nondestructive Characterization of Materials, Berlin, Germany, Jun. 2002.

Technical paper title "Application of MWM® Eddy-Current Technology during Production of Coated Gas Turbine Components," presented at 11th International Symposium on Nondestructive Characterization of Materials, Berlin, Germany; Jun. 2002.

Technical paper titled "Friction Stir Weld Inspection through Conductivity Imaging using Shaped Field MWM®-Arrays," presented at ASM Trends in Welding Conference, Callaway Gardens, GA; Apr. 2002.

Technical paper and presentation slides, titled "MWM-Array Characterization and Imaging of Combustion Turbine Components," presented at EPRI International Conference on Advances in Life Assessment and Optimization of Fossil Power Plants, Orlando, FL; Mar. 2002.

Technical paper titled "Surface Mounted and Scanning Periodic Field Eddy-Current Sensors for Structural Health Monitoring", presented at the IEEE Aerospace Conference, Mar. 2002.

Presentation slides titled "Corrosion Detection and Prioritization Using Scanning and Permanently Mountable MWM Eddy-Current Arrays," U.S. Army Corrosion Summit, Mar. 2002.

Technical paper and presentation slides titled "Shaped-Field Eddy-current Sensors and Arrays", SPIE 7th Annual International Symposium: NDE for Health Monitoring and Diagnostics, Mar. 2002.

Technical paper titled "Corrosion Detection and Prioritization Using Scanning and Permanently Mounted MWM Eddy-Current Arrays", Tri-Service Corrosion Conference, Jan. 2002.

Technical presentation slides "Condition Assessment of Engine Component Materials Using MWM Eddy-Current Sensors," ASNT Fall Conference, Columbus, OH; Oct. 2001.

Technical paper titled "Flexible Eddy Current Sensors and Scanning Arrays for Inspection of Steel and Alloy Components," 7th EPRI Steam Turbine/Generator Workshop and Vendor Exposition, Baltimore, MD; Aug. 2001.

Technical paper titled "Application for Conformable Eddy Current Sensors including High Resolution and Deep Penetration Sensor Arrays in Manufacturing and Power Generation," ASME 7th NDE Topical Conference, San Antonio, Texas; 2001.

* cited by examiner

HYBRID WOUND/ETCHED WINDING CONSTRUCTS FOR SCANNING AND MONITORING

RELATED APPLICATIONS

This application is a divisional of U.S. application Ser. No. 10/853,009, filed May 24, 2004, now abandoned which claims the benefit of U.S. Provisional Application No. 60/473,180 filed May 23, 2003 the entire teachings of which are incorporated herein by reference.

BACKGROUND OF THE INVENTION

This application relates to nondestructive materials characterization, particularly quantitative, model-based characterization of surface, near-surface, and bulk material condition for flat and curved parts or components using magnetic field based or eddy-current sensors. Characterization of bulk material condition typically includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing a material, such as alloy type, and material states, such as porosity and temperature. Characterization of surface and near-surface conditions includes measurements of surface roughness, displacement or changes in relative position, coating or material layer thickness, temperature and coating condition. Each of these characterization types includes detection of electromagnetic property changes associated with either microstructural and/or compositional changes, electronic structure (e.g., Fermi surface) or magnetic structure (e.g., domain orientation) changes, stress variations (e.g., in magnitude, orientation or distribution), or other features such as the presence of single or multiple cracks, inclusions, or localized corrosion.

Conventional eddy-current sensing involves the excitation of a conducting winding, the primary, with an electric current source of prescribed frequency. This produces a time-varying magnetic field, which in turn is detected with a sensing winding. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. In some cases, only the self-impedance of the primary winding is measured. Traditionally, scanning of eddy-current sensors across the material surface is then used to detect features, such as cracks.

In many inspection applications, large surface areas of a material need to be tested. This inspection can be accomplished with a single sensor and a two-dimensional scanner over the material surface. However, use of a single sensor has disadvantages in that the scanning can take an excessively long time and care must be taken when registering the measured values together to form a map or image of the properties. These shortcomings can be overcome by using an array of sensors, but each sensor must be driven sequentially in order to prevent cross-talk or cross-contamination between the sensors. An example is given in U.S. Pat. No. 5,047,719, which discloses the use of a flexible sensor arrays and a multiplexer circuit for measuring a response in the vicinity of each individual array element. Another example is given in U.S. Pat. No. 3,875,502 which discloses a single rectangular drive coil and multiple sense coils, including offset rows of sensing elements for complete coverage when scanned over a surface in a direction perpendicular to the longest segments of the drive coil. The sense coils are oriented in the vertical direction so that only the horizontal component of the magnetic flux is detected and measurement signal is non-negligible only when the sensor array is passed over a local anomaly. U.S. Pat. No. 5,793,206 provides another array example in which multiple sense elements are placed within a single sensor drive footprint. With known positions between each array element, the material can be scanned in a shorter period of time and the measured responses from each array element are spatially correlated. The teachings of the above three patents are incorporated by reference herein in their entirety.

In other inspection applications, there is a need to detect hidden flaws, such as cracks that form beneath fasteners, which means beneath the fastener head, nut, or washers used in the fastened joint. Often, the critical crack size for the structural element containing the fastener is small enough that the crack must be detected before it propagates from beneath the head or nut of the fastener. When the head is flush with the surface of the test material, sliding eddy current probes are commonly used in which the differential response between two coils is measured as the probe is scanned over the fastener. For protruding fastener heads or nuts, other electromagnetic techniques can be used which measure the response from a coil placed over the fastener, as described for example in U.S. Pat. No. 4,271,393, or from a coil mounted beneath a fastener head, as described, for example, in Great Britain Patent 886,247. Typically, the measured response is then compared to the response obtained on a reference sample with a fastener that contains a flaw of known size and has material properties and geometry that match the test material.

SUMMARY OF THE INVENTION

Aspects of the methods described herein involve novel sensors and sensor arrays for the measurement of the near surface properties of conducting and/or magnetic materials. These sensors and arrays use novel geometries for the primary winding and sensing elements that promote accurate modeling of the response and provide enhanced observability of property changes of the test material.

In one embodiment, a drive winding coil is formed with one or more turns using magnet wire (conducting wire with a thin insulating layer such as enamel). The winding is formed in a manner that the windings are either contained within a single plane or wound in a manner that the location of each turn is carefully controlled to permit an accurate prediction of the applied magnetic field using a model based method when an electric current is passed through the drive coil. The magnetic field is monitored using a linear array of micro-fabricated etched sensing elements that can be fabricated using etched or printed circuit manufacturing techniques. In a preferred embodiment, the sense elements are inductive coils, but other sensing elements such as magnetoresistive or giant magnetoresistive elements can also be used.

In an embodiment, the drive coil is attached to the same substrate as the sense elements using an adhesive. To help maintain the geometry of the drive coil a layer of material, which is preferably flexible, is first cut to the internal contour of the desired drive winding and attached to the adhesive. This contour can be any shape such as a an oval, circle, square with rounded edges, or an odd shape selected to support a specific component scanning, surface mounted, or embedded sensor development opportunity. The magnet wire or other conductor is then manually, semi-manually using fixtures or automatically using mechanical devices, placed one turn at a time on the adhesive around the internal guide so that first the innermost wire is laid down on the adhesive, which holds it in-place, and the location of each drive winding loop is well known.

The sensing element array is located at a controlled distance from the drive winding and is selected to provide the required sensitivity to buried features of interest or material properties of interest in the material under test or for an object imaging application. In one embodiment multiple sensing elements are located at varied distances or in multiple layers relative to the drive winding and in another embodiment the sense elements are oriented in different directions to provide sensitivity to multiple components of the magnetic field. The substrate for the sensor array may be flexible to provide conformability to the test material surface. In yet another embodiment, measurements can be performed at different lift-offs or proximities to the test material surface.

In an embodiment, the drive winding coil is located around a feature associated with the material under test, such as a fastener or a bolt. The drive is placed near the test material surface and can be placed around the fastener head or nut or between the test material surface and the fastener head or nut. The fabricated array of sense elements, which can be inductive, are then positioned or scanned around the fastener or positioned between other material layers or even on an opposing surface of the test material in the same region as the drive coil. The sense elements can be fabricated using etched or printed circuit manufacturing techniques, can be oriented to be sensitive to different components of the magnetic field, and in another embodiment, are located at varied radial distances from the drive coil. The substrate for the sense elements may be flexible to provide conformability to the test material surface and measurements can be performed at different lift-offs or proximities to the test material surface. The locations of the drive coil and sense elements could also be reversed, with the sense elements mounted under the fastener and the drive coil scanned or positioned around the fastener. Again, these embodiments can provide the desired observability to a feature or material property of interest, such as a buried crack, stress at an interface or stress in a bolt.

To improve the penetration of the magnetic field into the test material, a variety of methods are employed. In an embodiment, the drive coil is embedded in a material that supports the mechanical load but does not cause significant attenuation of the magnetic field from the drive coil. This is accomplished by making the support material from a relatively low electrical conductivity material, such as a composite, or splitting or laminating the support material to interrupt the flow of induced eddy currents. Similarly, the fastener itself could be split or the nut could be from a relatively low conductivity material. Standoffs can also be used which increase the distance between the nut and the drive coil. Another embodiment uses magnetizable materials in the support material, such as ferrites, to guide the magnetic flux as in a magnetic circuit. The magnetizable material can be coated onto the shaft of the fastener or inside of hollow fasteners.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
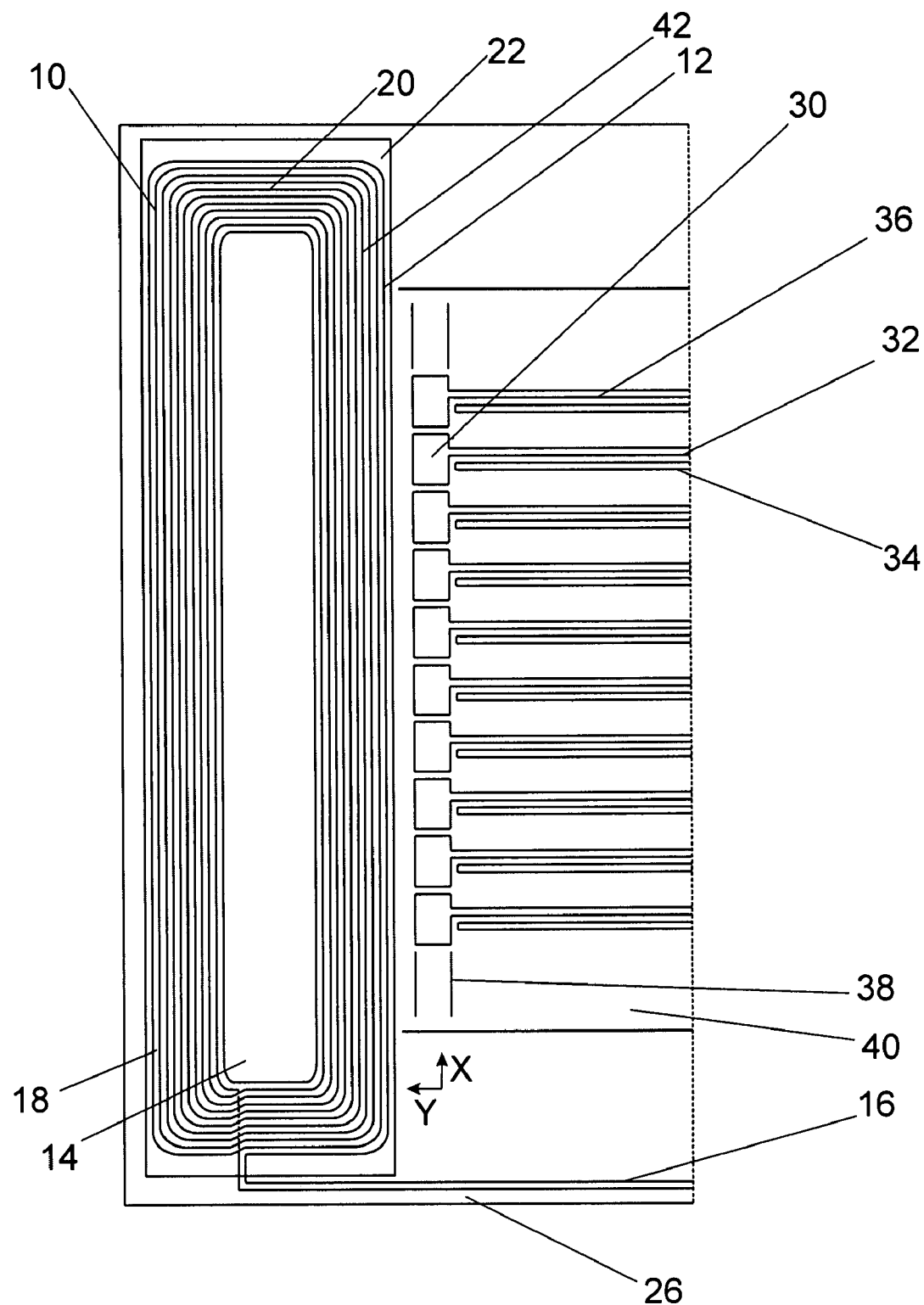
FIG. 1 is a drawing of a wound drive coil and an array of micro-fabricated sense elements.

A description of preferred embodiments of the invention follows.

The use of hybrid eddy-current sensors and sensor arrays is described herein for the nondestructive characterization of materials, particularly as it applies to the characterization of conducting and/or magnetic materials. This includes surface mounted and scanning, contact and non-contact configurations. This sensing approach can be used to monitor the material characteristics at a given location with single or multiple sensing element sensors, sensor arrays and/or networks of surface mounted sensors using hand-held probes, mounted into automated scanners or as part of an embedded network.

This invention describes the use of a combination of etched and wound winding constructs to construct an eddy current sensor or other inductive sensor, or a sensor with magnetic field measurement sensing element such as giant magnetoresistive (GMR) sensors, or with magnetic field (B field) and/or rate-of-field-change (dB/dt) sensing elements, or hybrid electroquasistatic (EQS)/magnetoquasistatic (MQS) sensors as disclosed in U.S. patent application Ser. No. 07/803,504 filed Dec. 6, 1991 and subsequently granted as U.S. Pat. No. 5,453, 689. That includes both inductive sensing elements and electrodes for measuring EQS field responses as well as inductive or B field measurement devices for MQS responses.

The combination of etched and wound constructs into a single sensor or sensor arrays combines the advantages of both construct types. Conventional eddy current sensors or sensor arrays using wound coils typically have high signal levels, due to the large number of turns in the coils, but do not provide predictable responses or responses that can be modeled accurately. As indicated by Auld and Moulder, for conventional eddy-current sensors "nominally identical probes have been found to give signals that differ by as much as 35%, even though the probe inductances were identical to better than 2%" Auld, B. A. and Moulder, J. C. (1999), "Review of Advances in Quantitative Eddy-Current Nondestructive Evaluation," Journal of Nondestructive Evaluation, vol. 18, No. 1 (from p. 23). The lack of reproducibility with conventional coils introduces severe requirements for calibration of the sensors (e.g., matched sensor/calibration block sets). Furthermore, during inspections, the drive and sense windings are typically at different and uncontrolled distances from the test material so that the response cannot be modeled accurately. In contrast, sensors or sensor arrays that are produced using micro-fabrication techniques typically employed in integrated circuit and flexible circuit manufacture have highly reliable and highly repeatable (i.e., essentially identical) sensors but only one or several winding turns. This results in signal levels that tend to be much smaller than wound coils, but the sensor response can be accurately modeled and predicted, which dramatically reduces calibration requirements. For example, in some situations an "air calibration" can be used to measure an absolute electrical conductivity without calibration standards. The hybrid constructs described here combine wound drive windings having well-known drive winding coil locations that allow the creation of larger magnetic fields than those typically found in micro-fabricated drive windings along with the well-defined repeatability of micro-fabricated sense elements. This hybrid design also accommodates a wider variety of test material and sensor geometries. The same sense element array can be used with many different drive winding constructs and the drive coils can be wound simply, even by hand, to the geometry of interest without incurring the full costs associated with the graphics and fabrication of a fully micro-fabricated sensor array.

FIG. 1 shows an embodiment of this invention and has a drive winding 10 formed from a wire coil and an array of sense elements 30 fabricated using standard micro-fabrication or etching techniques. The drive winding is formed with one or more turns using magnet wire or some other conducting wire with a thin insulating layer such as enamel. The sensor includes a primary winding 10 having extended portions for creating the magnetic field and secondary windings 30 for sensing the response. A current is applied to the primary winding to create a magnetic field and the response of the material under test (MUT) to the magnetic field is determined through the output response of each sense element. The winding is formed so that the coil turns are either contained within a single plane or wound in a manner that the location of each turn is carefully controlled. This careful control of the location of drive winding conductors allows the magnetic field created by current flow through the conductors to be accurately determined, which in turn allows the use of model based methods that can predict the response of the sensor variations in test material properties. An application of this type of model based method for sensors has been described in Re. 36,986 and U.S. Pat. No. 5,629,621, the entire teachings of which are incorporated herein by reference. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). A "planar" conformable eddy-current sensor, the Meandering Winding Magnetometer (MWM®), was designed to support these quantitative and autonomous data interpretation method and is described in U.S. Pat. Nos. 5,015,951, 5,453,689, and 5,793,206, the entire teachings of which are incorporated herein by reference. MWM sensors and MWM-Arrays can be used for a number of applications, including fatigue monitoring and inspection of structural components for detection of flaws, degradation and microstructural variations as well as for characterization of coatings and process-induced surface layers.

The sense elements 30 in FIG. 1 are fabricated using standard printed circuit manufacturing techniques and have a well-controlled geometry. These sense elements typically have a relatively small number of turns, ranging from one to several, with the interconnecting between the turns on individual layers made with vias. Connections 32 are made to each sense element so that the response of each element can be measured with appropriate instrumentation. An example parallel architecture impedance measurement instrument is described in U.S. patent application Ser. No. 10/155,887, filed on May 23, 2002, the entire teachings of which are incorporated herein by reference. Additional leads 34 that parallel the connection leads 32 to the sense elements but are shorted together near the sense elements can also be used. Subtracting the response of the additional leads 34 from the connection leads 32 effectively removes the signal contributions from stray flux passing through the connection leads. In addition, dummy elements 36 and leads that match the geometry of the sense elements can be placed at the ends of the array of sense elements to help to maintain the periodicity of the conducting segments and minimize end effect variations for the sense elements at the end of the array. Similarly, dummy conductors 38 can be placed at the ends of the arrays, as described in U.S. Pat. No. 6,188,218, the entire teachings of which are incorporated herein by reference. End effects can be further minimized by making the distance between the sense elements 30 and the return portions of the drive winding 20 large compared to the distance between the sense elements 30 and the adjacent portion of the drive winding 12. The sense elements are fabricated onto a substrate 40, which may be flexible material such as Kapton™, a polyimide available from E. I. DuPont de Nemours Company.

As shown in FIG. 1, a layer of flexible material 14, such as a plastic sheet commonly used for creating overhead transparencies, is cut to form the internal contour or shape for the winding. In this case, the drive winding has a rectangular geometry with extended segments 12 on two sides of the winding being substantially longer the segments 20 on the other sides of the winding. Other shapes are also possible such as a circle, square with rounded edges, a "D" shaped geometry that has a linear portion of the drive winding adjacent to the sense elements 30 and a semi-circular or elliptical return portion for the windings, or an odd shape selected to support a specific component scanning, surface mounted, or embedded sensor development opportunity. In one embodiment, the drive winding is constructed by applying an adhesive layer to the substrate 40 for the sense element array and attaching the contour sheet to the adhesive. The magnet wire or other conductor is then manually, semi-manually using fixtures or automatically using mechanical devices, placed one turn at a time on the adhesive around the cut internal or contour guide so that first the innermost wire is laid down on the adhesive, which holds it in-place. Then each successive winding is applied and attached to the adhesive. FIG. 1 shows a 10 turn "race track" design. The leads 16 are then connected to the electrical source circuitry and instrumentation. With the locations of the coil windings known accurately and the sense element geometry and positions also known accurately, the response can be accurately modeled using two-dimensional and three-dimensional modeling methods, including analytical methods or numerical methods such as finite element or boundary element methods.

FIG. 1 also shows some alternative formats for the test circuit. For example, the drive winding 10 can be fabricated onto its own substrate 22. The drive winding substrate is then attached directly to the sense element substrate 40 or to another substrate material 26 that is also attached to the sense element substrate 40.

The sensing element array is located at a controlled distance from the drive winding as shown in FIG. 1 as the distance between the sense elements 30 and the adjacent portion of the drive winding 12. This distance is selected to provide the required sensitivity to buried features or material properties of interest in the MUT or for an object imaging application. Preferably the width 42 of the drive coil windings is small compared to this distance. In an embodiment, the sensing element array is located approximately one-half of the width of the drive winding loop away from the drive winding loops. Defining the width of the drive loop as a half-wavelength, this makes the sense element array distance to the drive winding a quarter-wavelength. Additional sensing elements can be located at varied distances to the drive winding or in multiple layers relative to the drive winding to provide improved observability of a property or feature of interest.

Figure 2:
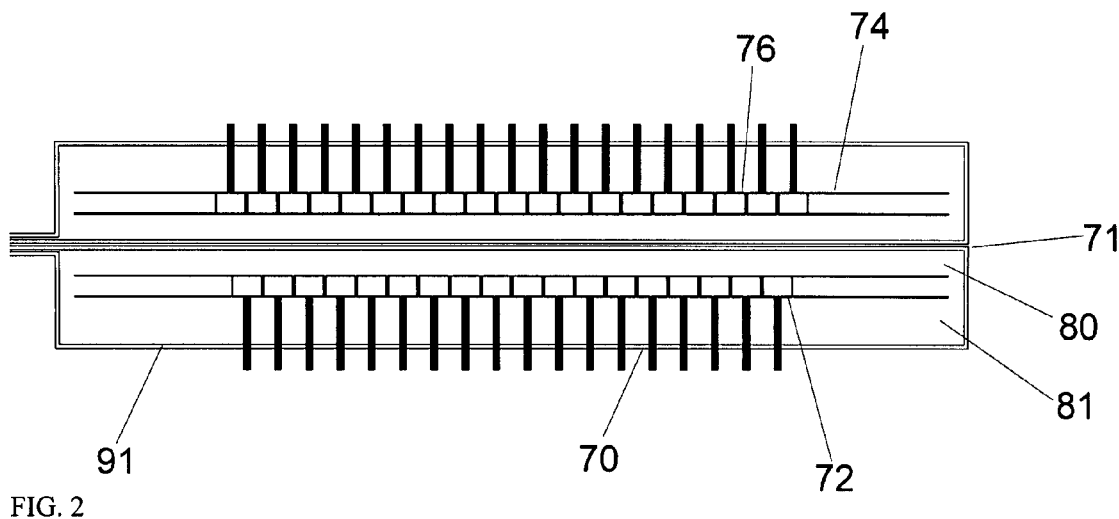
FIG. 2 is an expanded view of the drive winding and sense elements for an eddy-current array having offset rows of sensing elements.
Figure 3:
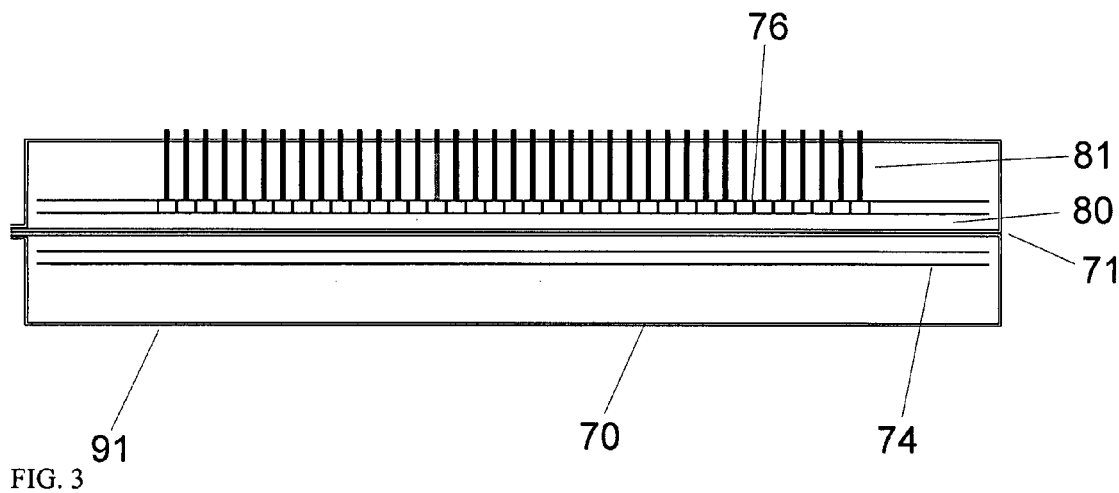
FIG. 3 is an expanded view of the drive winding and sense elements for an eddy-current array having a single row of sensing elements.
Figure 4:
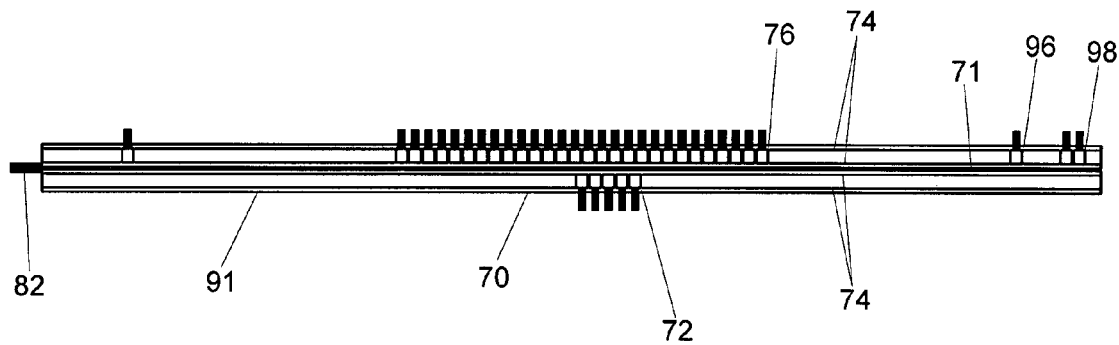
FIG. 4 is an expanded view of an eddy-current array where the locations of the sensing elements along the array are staggered.

Example sensor arrays are shown in FIG. 2 through FIG. 4 some embodiments of which are described in detail in U.S. patent application Ser. No. 10/102,620, filed Mar. 19, 2002, and Ser. No. 10/155,887, filed May 23, 2002, the entire teachings of which are incorporated herein by reference. These arrays include a wound coil primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218. When the sensor is scanned or when a feature (or object) propagates across the sensor, perpendicular to the extended portions of the primary winding, secondary elements 72 in a primary winding loop adjacent to the first array of sense elements 76 provide a complementary measurement. Also, the sensor may be rotated or tilted relative to the object. These arrays of secondary elements 72 can be aligned with the first array of elements 76 so that images of the material properties will be duplicated by the second array. Note that improving the signal-to-noise through combining the responses or providing sensitivity on opposite sides of a feature such as a fastener is described in U.S. patent application Ser. Nos. 10/102,620 and 10/155,887. Alternatively, to provide complete coverage when the sensor is scanned across a part the sensing elements, can be offset along the length of the primary loop perpendicular to the extended portions of the primary winding, as illustrated in FIG. 2.

The dimensions for the sensor array geometry and the placement of the sensing elements can be adjusted to improve sensitivity for a specific inspection. For example, the effective spatial wavelength or four times the distance 80 between the central windings 71 and the sensing elements 72 can be altered to adjust the sensitivity of a measurement for a particular inspection. For the sensor array of FIG. 2, the distance 80 between the secondary elements 72 and the central windings 71 is smaller than the distance 81 between the sensing elements 72 and the return windings 91. An optimum response can be determined with models, empirically, or with some combination of the two. An example of a modified sensor design is shown FIG. 3. In this sensor array, all of the sensing elements 76 are on one side of the central drive windings 71. The size of the sensing elements and the gap distance 80 to the central drive windings 71 are the same as in the sensor array of FIG. 2. However, the distance 81 to the return of the drive winding has been increased, as has the drive winding width to accommodate the additional elements in the single row of elements. Increasing the distance to the return reduces the size of the response when the return crosses a feature of interest such as a crack. Another example of a modified design is shown in FIG. 4. Here, most of the sensing elements 76 are located in a single row to provide the basic image of the material properties. A small number of sensing elements 72 are offset from this row to create a higher image resolution in a specific location. Other sensing elements are distant from the main grouping of sensing elements at the center of the drive windings to measure relatively distant material properties, such as the base material properties for plates at a lap joint or a weld.

Figure 5:
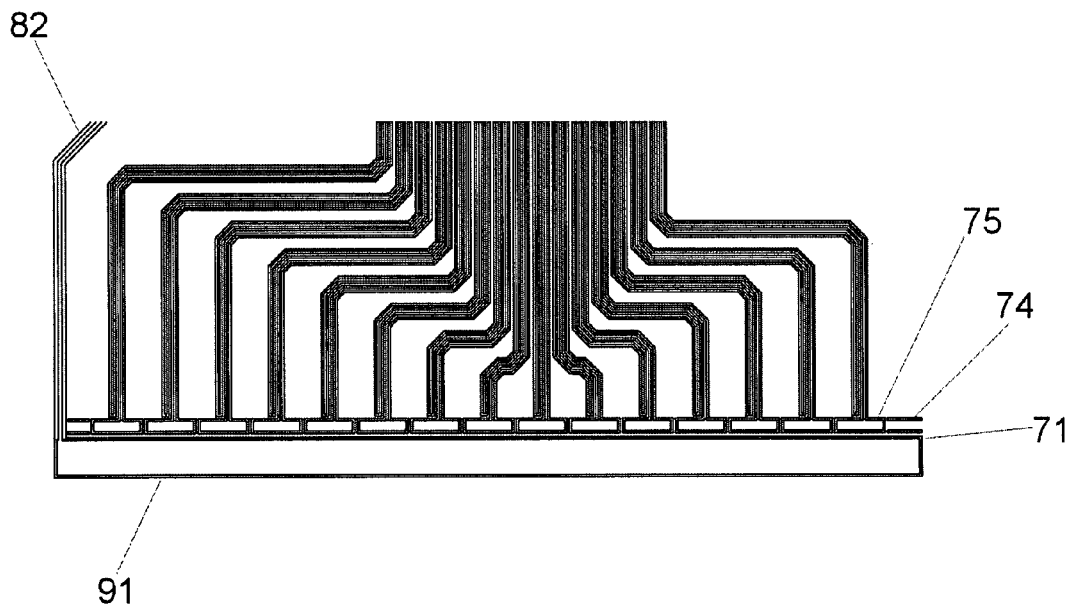
FIG. 5 is an expanded view of an eddy current array with a single rectangular loop drive winding and a linear row of sense elements on the outside of the extended portion of the loop.

In an embodiment, the number of windings used in the primary winding can be reduced further so that a single rectangular drive is used. As shown in FIG. 5, a single winding loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. In one embodiment this distance is optimized using models to maximize sensitivity to a feature of interest such as a buried crack or stress at a specific depth. Advantages of the design in FIG. 5 include a narrow drive and sense structure that allows measurements close to material edges and non-crossing winding pathways so that a single layer design can be used with all of the conductors in the sensing region in the same plane. In another embodiment additional rows of sense elements can be placed on the opposite side of the drive 71 at the same or different distances from the drive. In another embodiment sensing elements can be placed in different layers to provide multiple lift-offs at the same or different positions.

Figure 6:
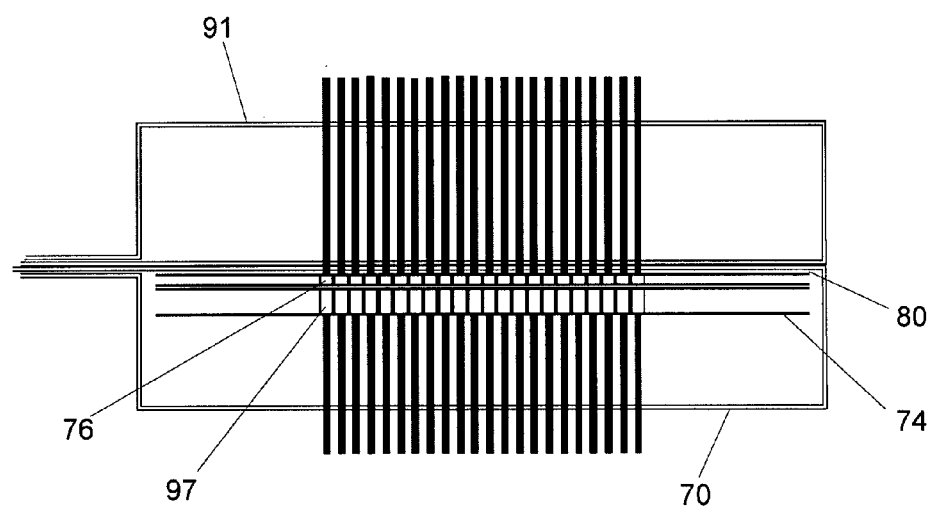
FIG. 6 is an expanded view of an eddy current array with a dual rectangular loop drive winding and two rows of sense elements at different distances to the drive winding.

In another embodiment, sense elements are placed at different distances to the drive winding to sample different portions of the magnetic field in a segmented field manner. The sense elements further from the drive winding sample magnetic fields that tend to penetrate deeper into the test material so that sense elements at different distances to the drive winding sample different segments of the magnetic field. One example array, shown in FIG. 6 and described in U.S. patent application Ser. No. 10/155,887, filed on May 23, 2002, and Ser. No. 10/454,383, filed on the Jun. 3, 2003, the entire teachings of which are incorporated herein by reference, has a second array of sense elements 97 further from the central drive windings than the first array of sense elements 76. In this case, in order to make connections to the individual sense elements, the leads to the sense elements are in a different plane than the primary winding. Also in this case the elements 97 are larger than the elements 76 so that the both sets of elements would link the same amount of magnetic flux when the sensor array is in air as the magnetic field decays with distance from the primary winding windings. As a further alternative, other sensing elements such as GMR sensors that respond to the magnetic field could be used as the sense elements that are further away from the primary winding. These elements may provide more sensitivity to the field, particularly at low frequencies, than similar sized inductive coils, which respond to the time rate of change of the magnetic flux through the coil. In some cases, the combination of inductive coils near the primary winding and GMR sensors further away can provide the segmented field sensing capability with the greatest sensitivity to the magnetic field. Of course other types of one-dimensional or two-dimensional arrays of sense elements could also be used. This includes orienting one or more of the sense elements to be sensitive to other components of the magnetic field.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation. The database could also include other properties or parameters of interest, such as the damage conditions or even the progression of these damage conditions, for rapid assessment and decision support purposes.

Figure 7:
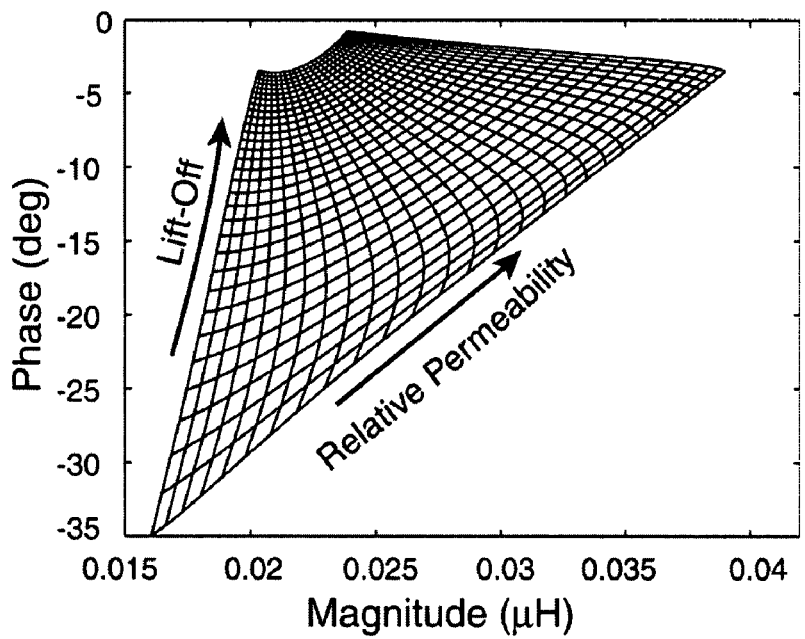
FIG. 7 shows a representative measurement grid relating the magnitude and phase of the sensor terminal impedance to the lift-off and magnetic permeability.
Figure 8:
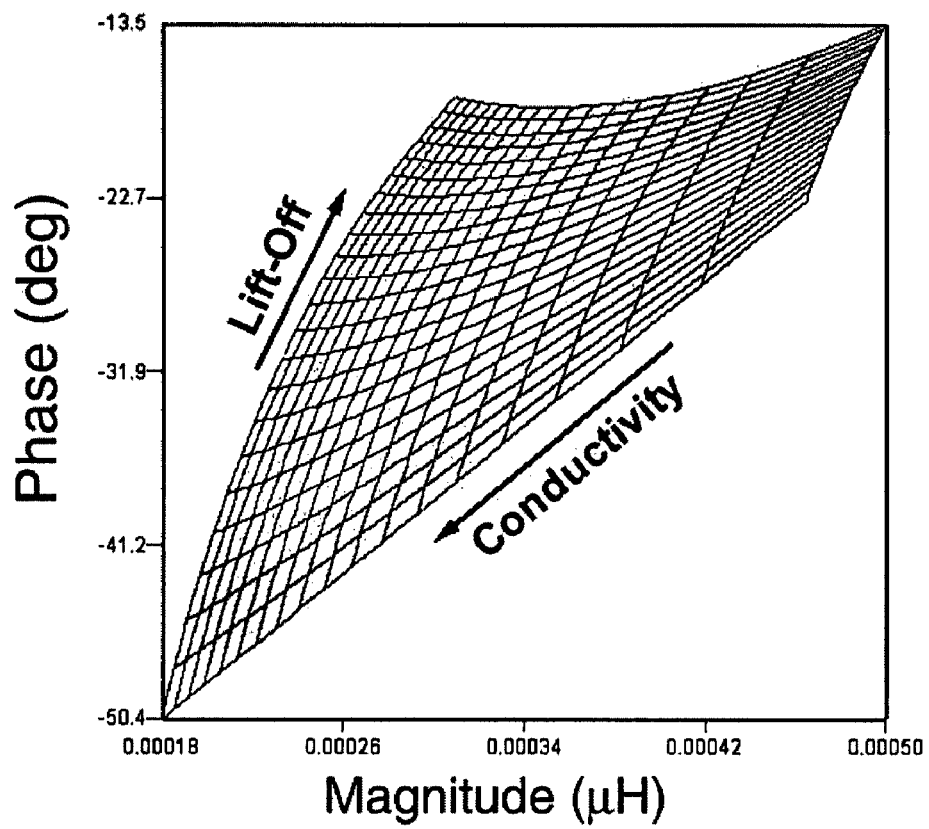
FIG. 8 shows a representative measurement grid relating the magnitude and phase of the sensor terminal impedance to the lift-off and electrical conductivity.

For ferromagnetic materials, such as most steels, a measurement grid provides conversion of raw data to magnetic permeability and lift-off. A representative measurement grid for ferromagnetic materials (e.g., carbon and alloy steels) is illustrated in FIG. 7. A representative measurement grid for a low-conductivity nonmagnetic alloy (e.g., titanium alloys, some superalloys, and austenitic stainless steels) is illustrated in FIG. 8. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest.

The properties or responses that are measured with the sense can also be compared to a training set of components, e.g., with varied stress distributions with depth, or with varied temperature or with varied crack sizes or object features, to develop a correlation relationship. In practice the measurements are related to absolute properties and to the correlated properties or features of interest. Alternatively, the measurements can be directly related to the properties or features of interest without conversion to absolute properties. In addition, spatial distributions of responses in one or more dimension are used from training set samples or using models to derive filters or signatures that are later used to process scans or images to identify features or objects of interest and suppress clutter of background. In another embodiment, the statistics or characteristics of the background are used to set thresholds for anomaly detection or identification of indications of interest. These alternatives are described in U.S. patent application Ser. No. 10/102,620, filed Mar. 19, 2002, and Ser. No. 10/155,887, filed May 23, 2002.

An application of these types of sensor arrays is the detection, characterization, and imaging of hidden or buried features such as corrosion. As part of the characterization, the material loss or other geometric features or properties associated with the corrosion are to be estimated. This can be accomplished using measurement grids with a calibration either in air or on reference parts along with means for scanning the array over the test material. Means for encoding and recording the position of the array may also be used so that the images have defined spatial dimensions.

Figure 9:
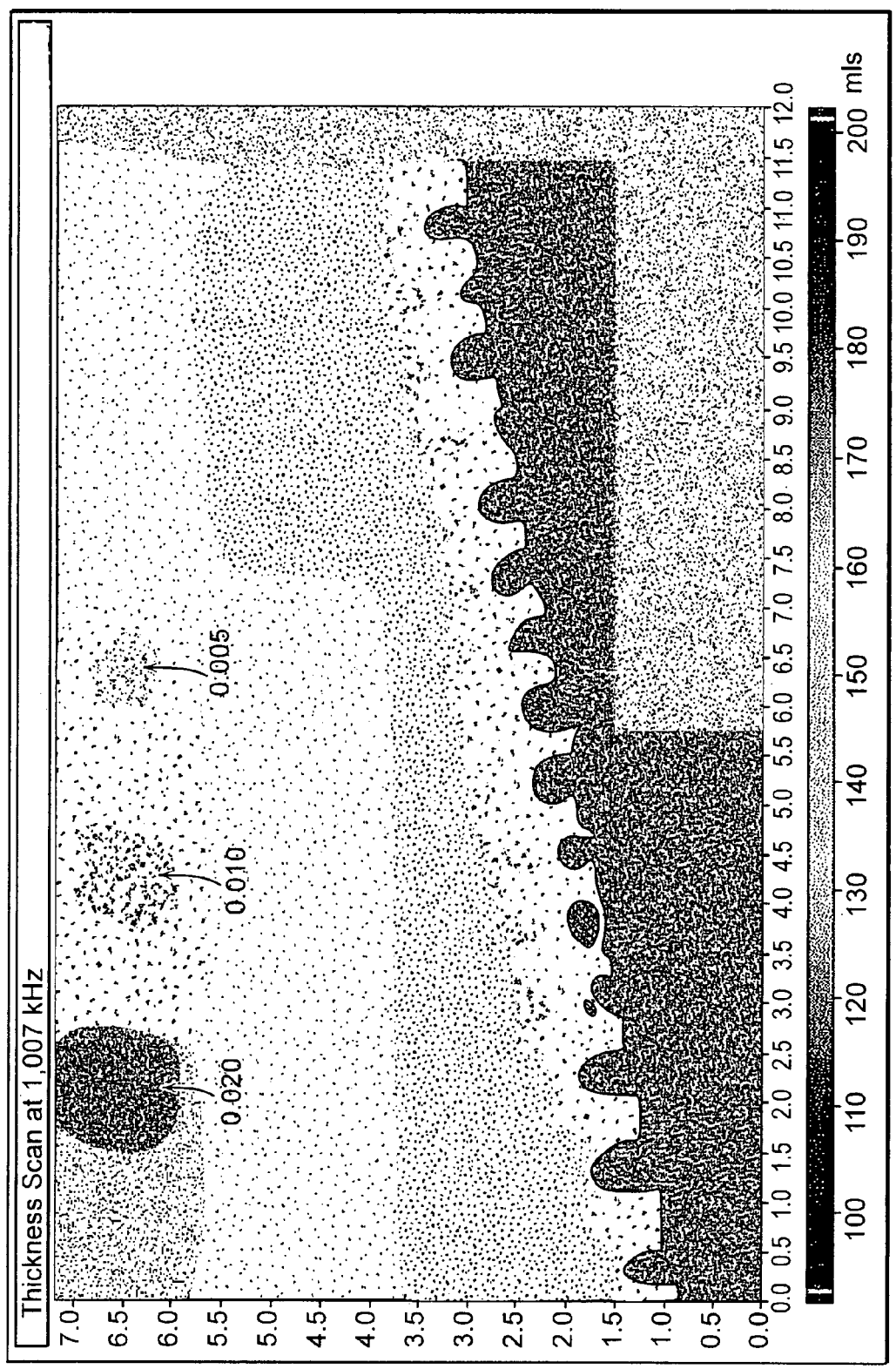
FIG. 9 is a representative scan image of wing plank remaining material thickness with milled out regions to simulate material loss.

FIG. 9 shows an example image obtained from an inspection of a wing plank for hidden corrosion damage. Three regions were milled out in this wing plank to simulate corrosion loss of approximately 0.005, 0.010 and 0.020 in. deep on the back side. The corresponding values for the maximum material loss depth estimate obtained with the hybrid sensor array for the milled out regions are 0.004, 0.011, and 0.022 inches, respectively, which are in good agreement with the actual depths measures with a depth gauge. The image also shows the basic thickness variations along different sections of the plank and semi-circular indications that correspond to fastener holes near the edge of the plank.

Figure 10A:
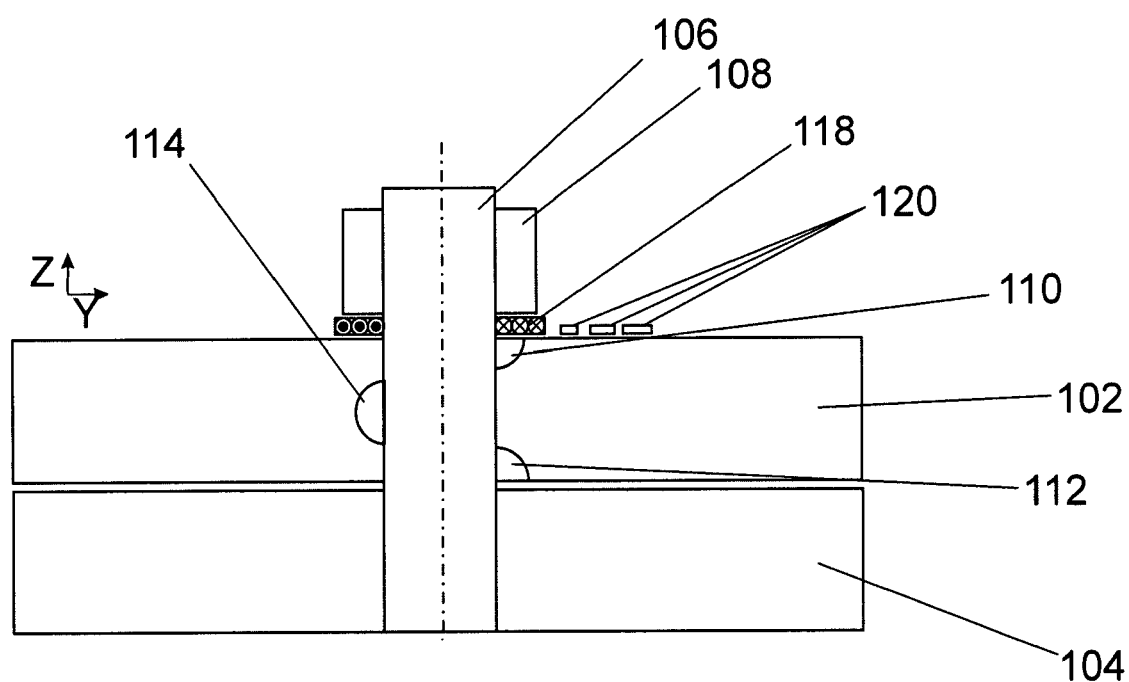
FIG. 10A shows a cross-sectional schematic view of a simple drive washer around a fastener and between a nut and material layer. Potential flaw locations in the upper layer are indicated.
Figure 10B:
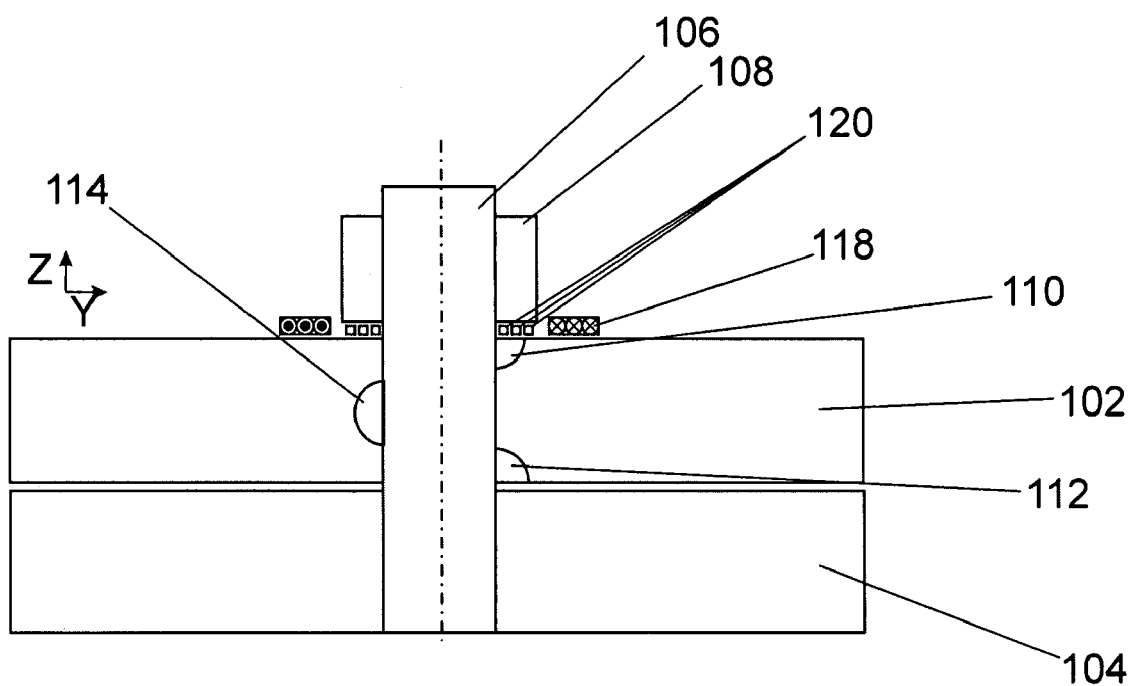
FIG. 10B shows a cross-sectional schematic view of a simple drive washer around the outside of a fastener and sense elements between a nut and material layer.
Figure 11A:
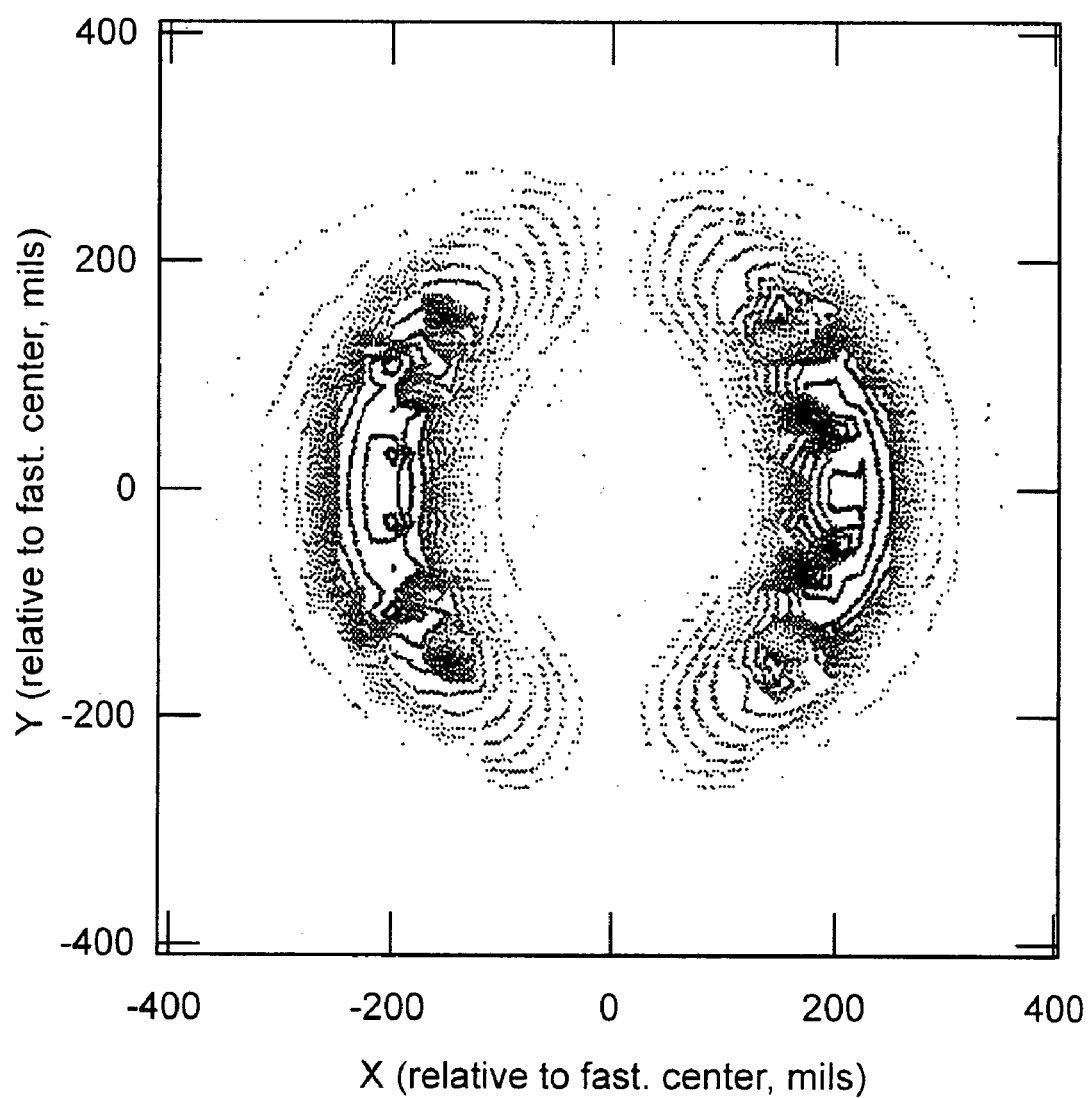
FIG. 11A shows a contour plot of the x component of the magnetic field intensity along the material layer surface for a simple drive washer under a fastener nut.
Figure 11B:
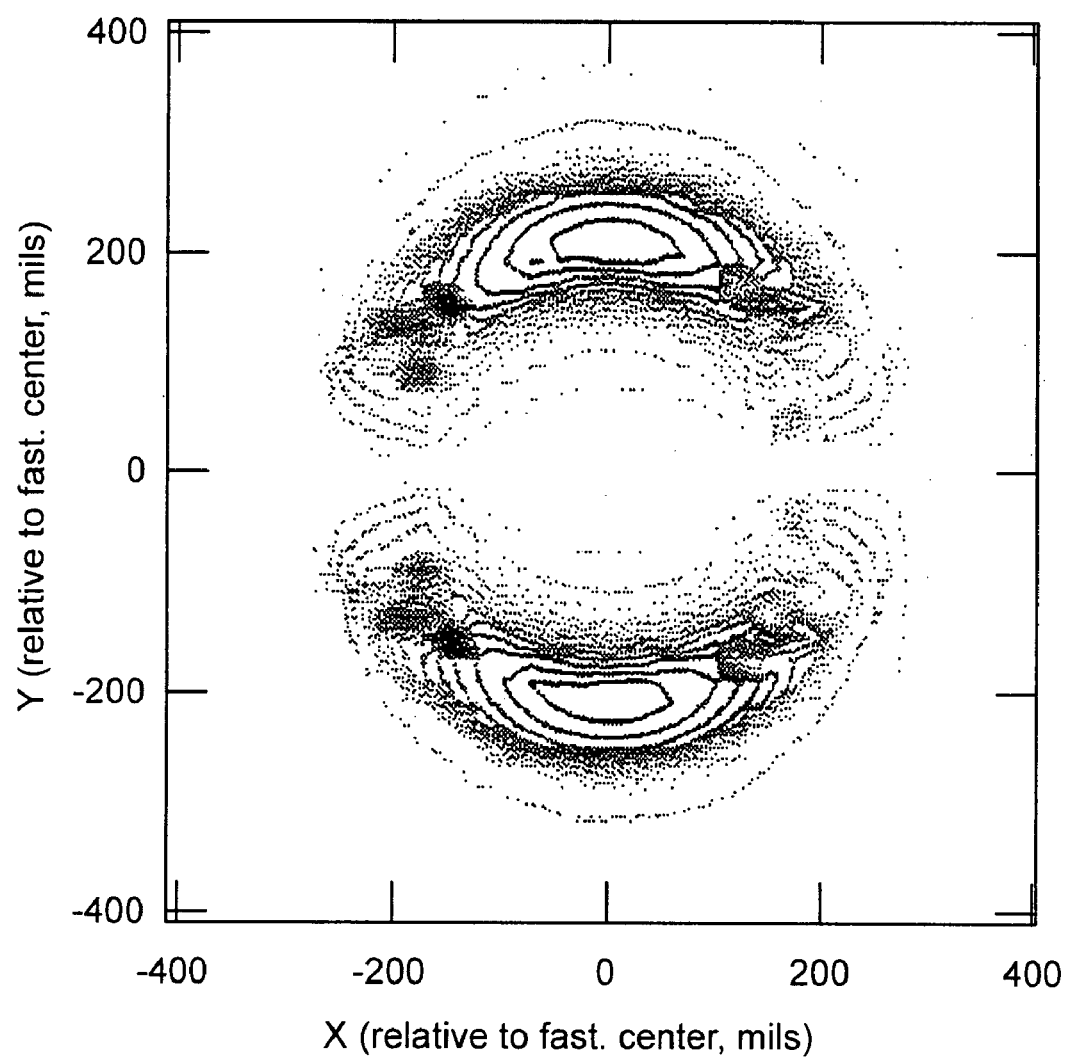
FIG. 11B shows a contour plot of the y component of the magnetic field intensity along the material layer surface for a simple drive washer under a fastener nut.
Figure 11C:
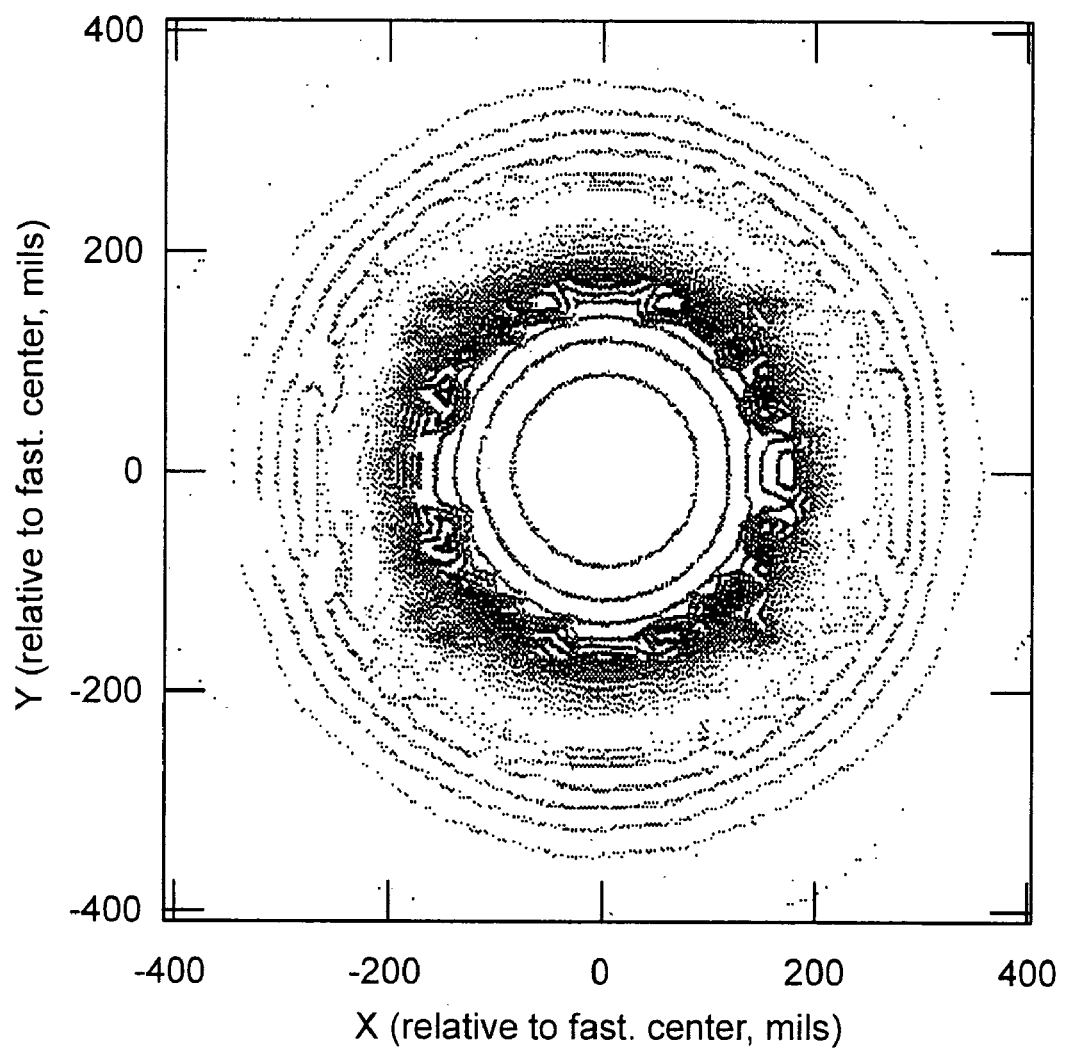
FIG. 11C shows a contour plot of the z component of the magnetic field intensity along the material layer surface for a simple drive washer under a fastener nut.
Figure 12A:
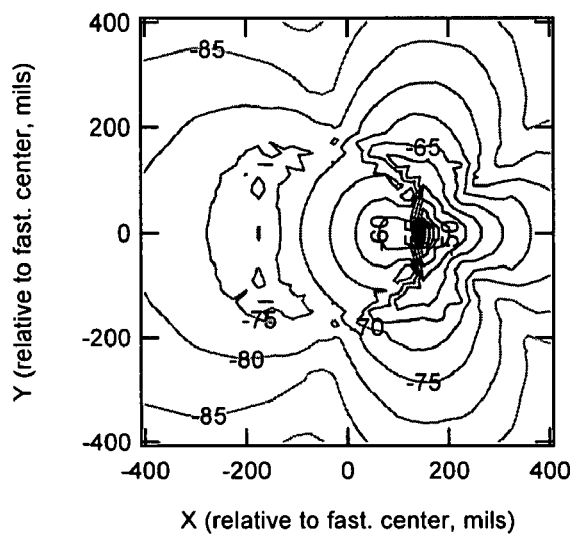
FIG. 12A shows a contour plot of the x component of the perturbation of the magnetic field intensity in dB for a flaw under a fastener nut at the top of the upper aluminum layer and a simple drive washer.
Figure 12B:
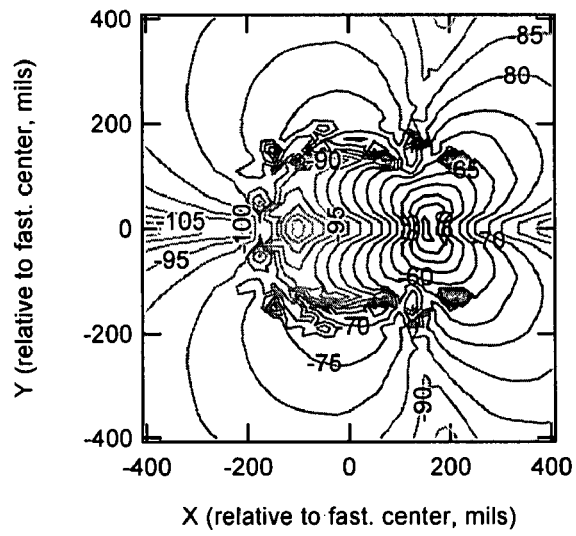
FIG. 12B shows a contour plot of the y component of the perturbation of the magnetic field intensity in dB for a flaw under a fastener nut at the top of the upper aluminum layer and a simple drive washer.
Figure 12C:
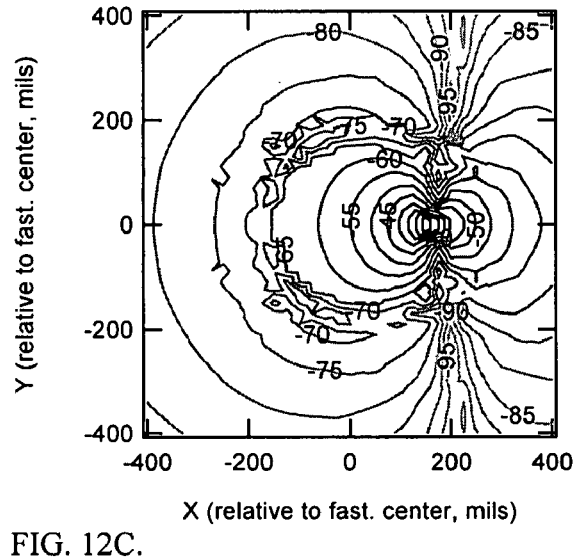
FIG. 12C shows a contour plot of the z component of the perturbation of the magnetic field intensity in dB for a flaw under a fastener nut at the top of the upper aluminum layer and a simple drive washer.
Figure 13A:
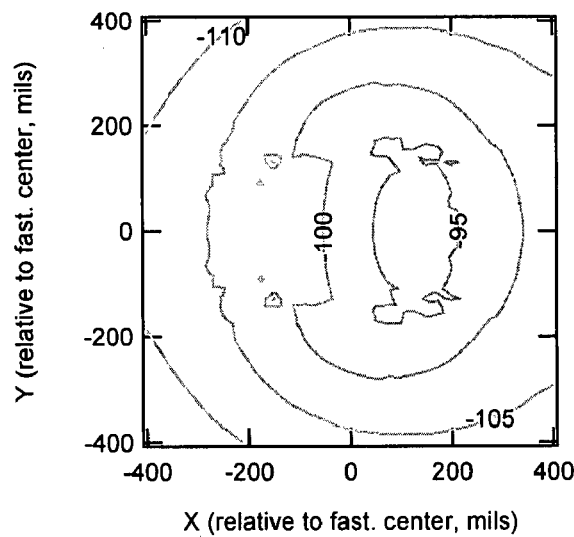
FIG. 13A shows a contour plot of the x component of the perturbation of the magnetic field intensity in dB for a flaw under a fastener nut at the bottom of the upper aluminum layer and a simple drive washer.
Figure 13B:
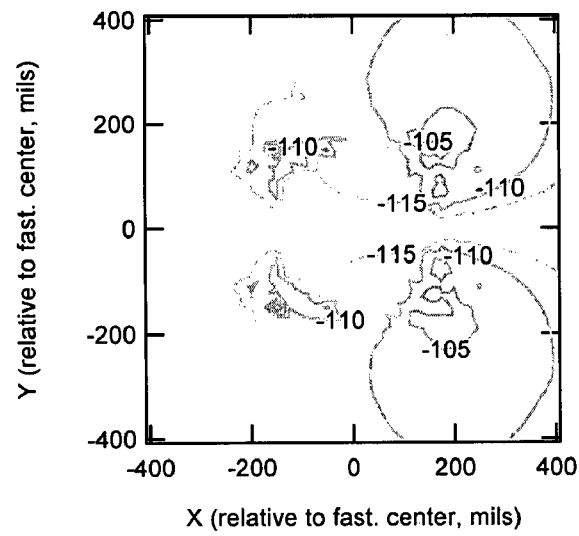
FIG. 13B shows a contour plot of the y component of the perturbation of the magnetic field intensity in dB for a flaw under a fastener nut at the bottom of the upper aluminum layer and a simple drive washer.
Figure 13C:
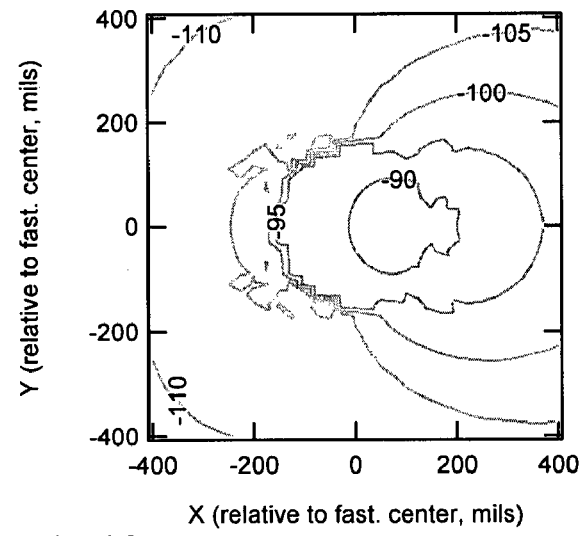
FIG. 13C shows a contour plot of the z component of the perturbation of the magnetic field intensity in dB for a flaw under a fastener nut at the bottom of the upper aluminum layer and a simple drive washer.

This type of sensor construct can also be used for inspecting in the vicinity of features. An example of which is having drive windings formed around a material under test feature such as a bolt or the shaft of a fastener. FIG. 10 shows one such application of this type of design. A 0.312-inch diameter titanium fastener 106 is passed through a 0.350-inch thick upper aluminum layer 102 and a 0.500-inch thick lower aluminum layer. An aluminum nut 108 (0.538-inch diameter and 0.350-inches tall) holds the layers together but the fastener head is not shown. In this particular geometry, cracks form in the bolt hole in the upper layer at the top 110, bottom 112, or middle 114 locations in the layer and there is a need to detect the cracks while they are still hidden beneath the fastener nut. FIG. 10 shows one hybrid implementation in which a wound coil 118 is embedded into a support material, such as a composite or an epoxy material, in the form of a cylindrical shape or washer. This washer construct must withstand the mechanical load required for the fastener and driving the coil with an electrical current can create a magnetic field. Placing sense elements 120 around the fastener then allows the presence of the cracks to be determined. Sense elements can be placed at different distances to the drive coil to detect perturbations in different segments of the magnetic field, as described in FIG. 5 for the segmented field approach The geometry shown in the schematic of FIG. 10 was simulated with a three-dimensional model. The simulations included an unflawed layer, crack 110, and crack 112. When present the crack was assumed to be 0.050-inches long. An excitation frequency of 100 Hz was selected and the drive coil was driven as 1 A-turn. The corresponding magnitude of the magnetic field intensity at a height of 0.0025-inches over the surface of the test material is shown in the contour plots of FIGS. 11A, 11B, and 11C. As expected for this winding geometry, the field has circular symmetry, with the x and y components only reflecting a portion of the radial field. FIGS. 12A, 12B, and 12C show the perturbation in the magnetic field intensity over the surface of the test material due to the presence of a crack in the top of the upper layer. This perturbation for each field component is expressed in dB as $20 \log_{10}(dH/H_{peak})$ where dH is the magnitude of the differential change in the complex magnetic field between the flawed and flawed simulations and the $H_{peak}$ is the magnitude of the peak field intensity in the unflawed simulation. These dipole-type field patterns are concentrated in the vicinity of the crack and indicate that, in this case, the z component is most sensitive to the crack presence. The placement of sensing elements throughout the perturbation field pattern and at different orientations can provide complementary information about the crack position and size. FIGS. 13A, 13B, and 13C show similar perturbations in the magnetic field intensity due to the presence of a crack in the bottom of the upper layer, except that the signal size is significantly smaller.

Figure 14:
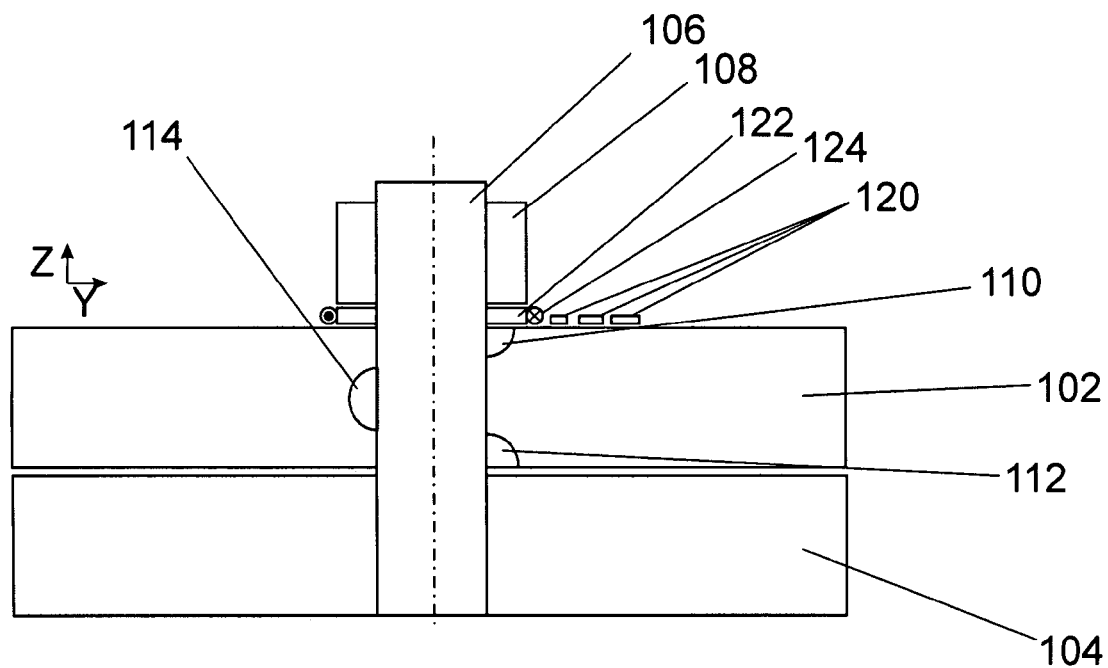
FIG. 14 shows a cross-sectional schematic view of a drive winding and a support washer around a fastener and between a nut and material layer. Potential flaw locations in the upper layer are indicated.
Figure 15:
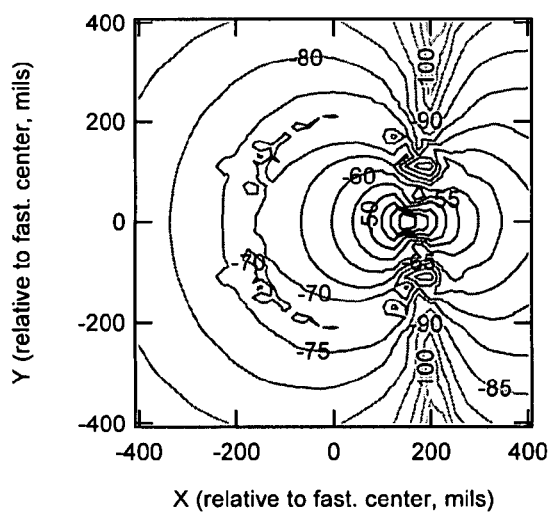
FIG. 15 shows a contour plot of the z component of the perturbation of the magnetic field intensity in dB for a flaw under a fastener nut at the top of the upper aluminum layer and a drive/aluminum washer.
Figure 16:
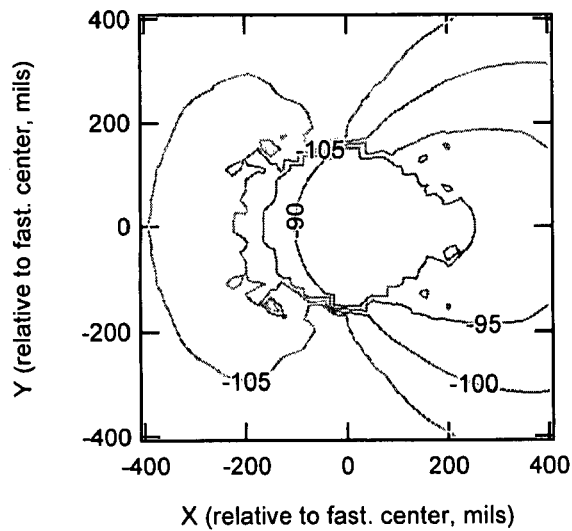
FIG. 16 shows a contour plot of the z component of the perturbation of the magnetic field intensity in dB for a flaw under a fastener nut at the bottom of the upper aluminum layer and a drive/aluminum washer.

FIG. 14 shows another hybrid sensor implementation around a fastener. In this case the washer of support material 122 is placed directly under the nut and a drive winding coil 124 is placed around the outside of the washer. This provides similar field patterns as the geometry of FIG. 10. FIG. 15 shows the perturbation field when the support material is an aluminum washer and the crack is at the top of the upper layer. FIG. 16 shows the corresponding plot for the crack at the bottom of the upper layer. Similar results are obtained for a titanium washer support material, indicating that at these frequencies the magnetic field from the drive coil is not being substantially attenuated by the washer material. FIG. 15 shows a slight improvement in the response compared to FIG. 12C, because a larger fraction of the magnetic field is focused near the vicinity of the crack tip. Improvements in the response can also be obtained by introducing insulating or low conductivity space materials between the nut (or fastener head) and the test material. This has the effect of reducing the shielding of the nut on both the imposed magnetic field and the perturbations in the magnetic field caused by the flaw.

Figure 17:
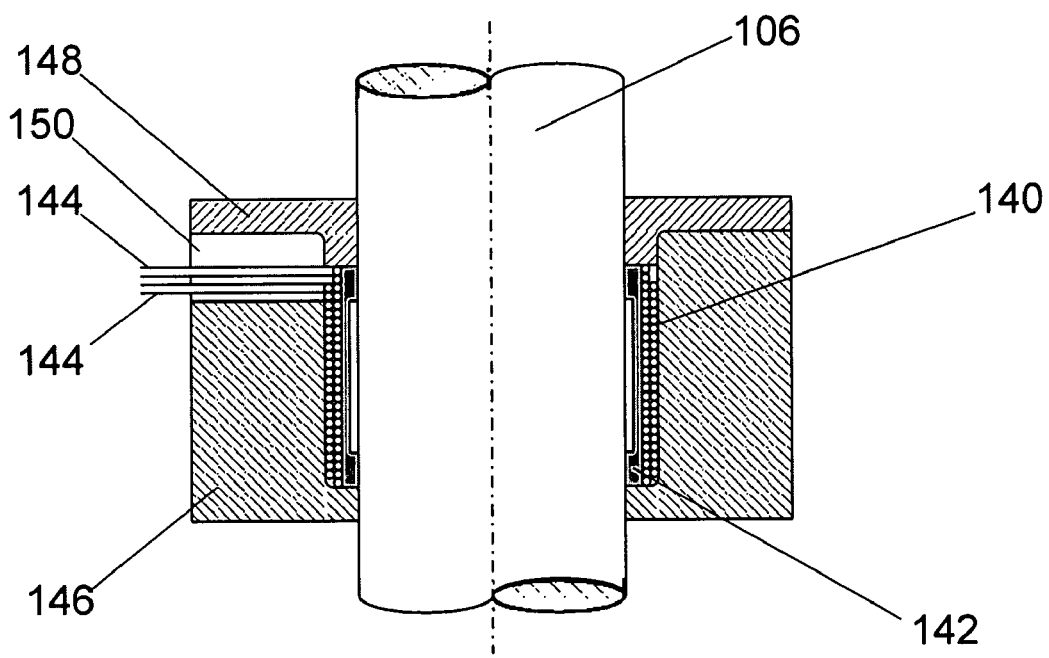
FIG. 17 shows a cross-sectional schematic view of a drive winding coil embedded in a support washer.

Another method for improving the sensitivity to the hidden cracks includes embedding the drive into the support washer as shown in FIG. 17. The drive winding coil 140, having numerous winding turns or loops with the location of each winding loop being well known, is mounted onto a support sleeve 142 for ease of manufacture. This support sleeve could simply be a thin walled tubing so that the drive coil is wound as a simple solenoid. The drive coil is then inserted into the center portion of a lower support material 146 and capped by an upper support material 148. The support materials can be relatively low conductivity metals, such as titanium, that should not significantly prevent the magnetic field from passing into the test material. The support materials could also be composite or epoxy layers, as long as they are able to withstand the mechanical load and would not contribute to corrosion around the fastener. The lower support material 146 also has an access groove 150 which allows access to the electrical leads 144 of the drive coil.

Figure 18:
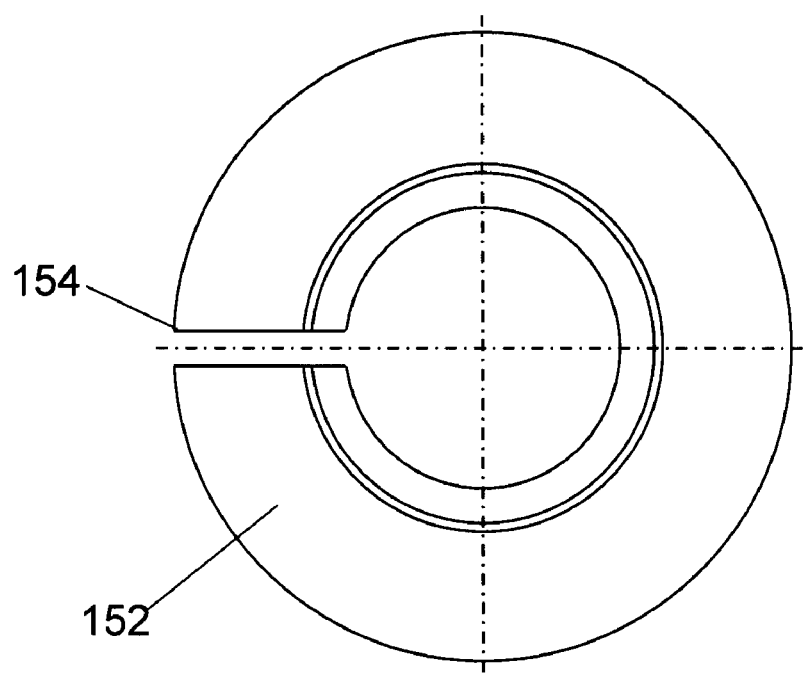
FIG. 18 shows a top view of a split support material for a drive winding washer.

The support materials, or even the fastener shaft, head, and nut, can be modified if they cause significant attenuation of the magnetic field created by the drive coil. For example, the materials may be laminated, as is commonly done with transformer cores, or split to interrupt the flow of induced eddy currents. For example, FIG. 18 shows a lower support material 152 that has a split 154. Since the eddy currents induced in the support material will tend to flow in the same direction as the current in the drive coil, which is circumferential in this case, the split in the support material interrupts the induced current flow and reduces the attenuation of the magnetic field that passes through the support material. This effect is most significant at excitation frequencies where the skin depth is comparable to or smaller than the thickness of the support material. Similar to FIG. 17, the electrical leads to the drive coil can be passed through this split and, appropriate, a split can be introduced into the upper portion of the support material. Furthermore the fastener shaft or nut may also be split.

Figure 19:
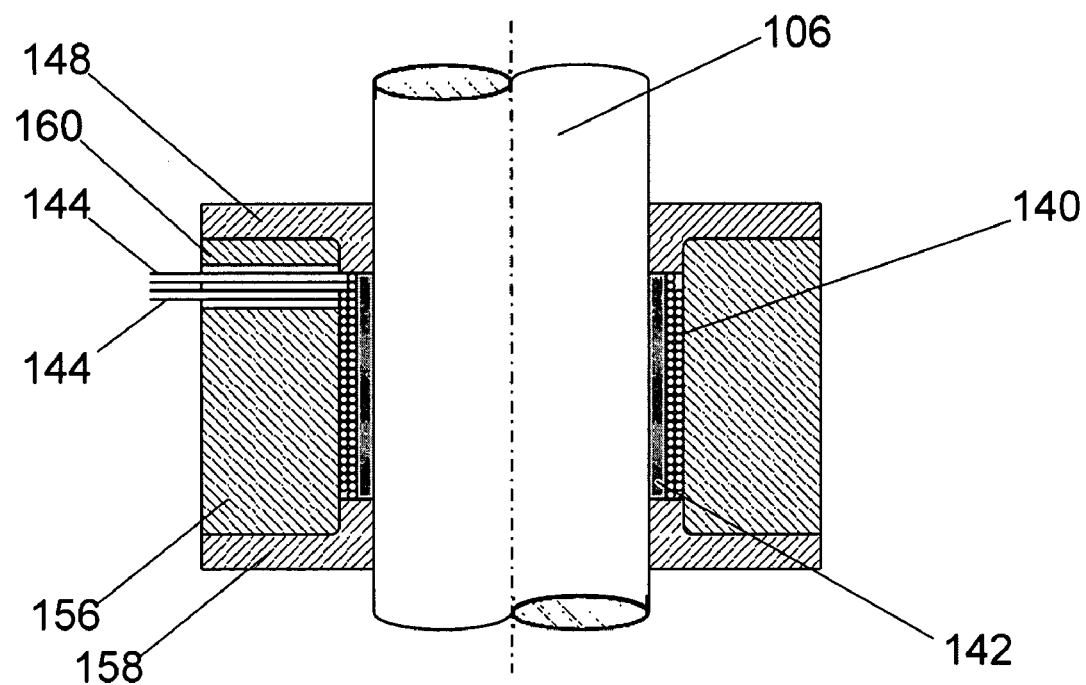
FIG. 19 shows a cross-sectional schematic view of a drive winding coil embedded in a support washer.

FIG. 19 shows another variation of the drive washer design. The lower support material is divided into a bottom support 158 that has the same shape as the upper support material 148. A cylindrical shaped washer 156 holds the drive coil in place and carries the mechanical load between the upper and bottom supports. A hole 160 is made in the cylindrical washer 156 to allow access to the drive coil leads.

Figure 20:
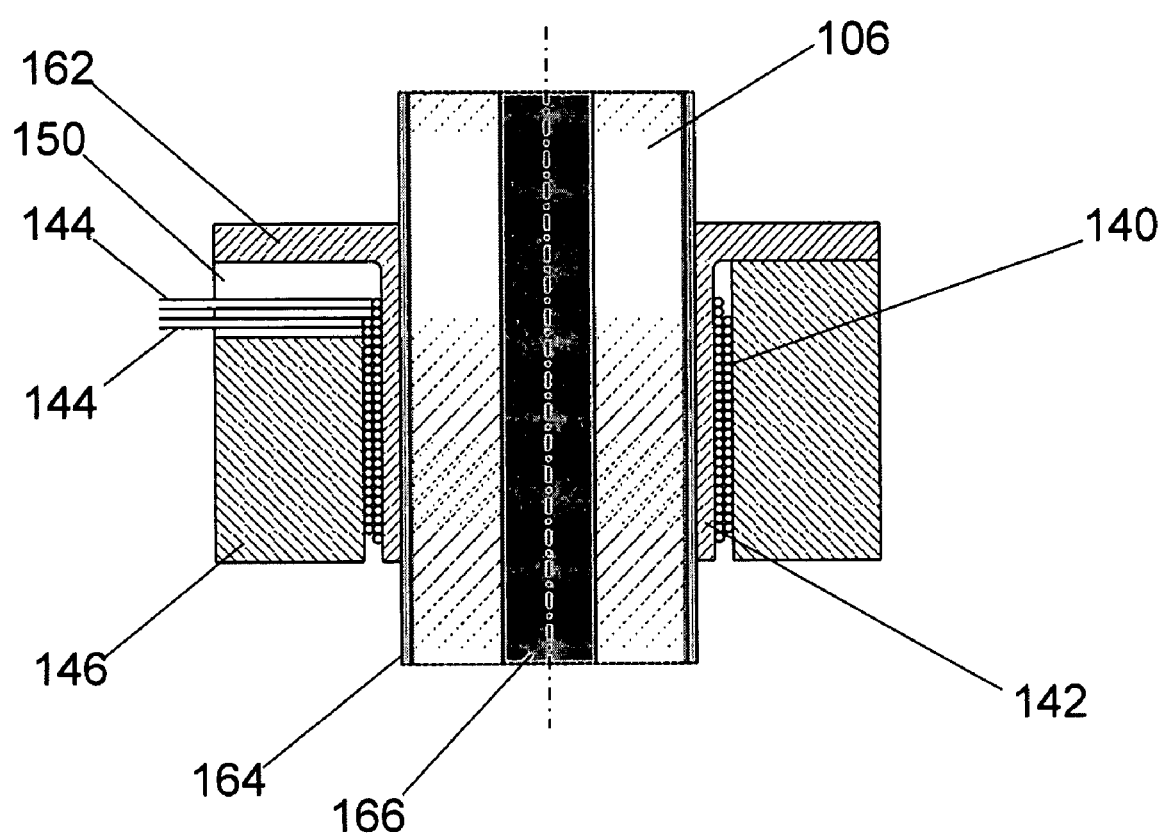
FIG. 20 shows a cross-sectional schematic view of a drive winding coil inside a support washer and magnetizable material in the fastener.

FIG. 20 shows yet another variation of the drive washer design and also some modifications that can be made to the fastener itself. In this case the upper support 162 has a relatively long cylindrical portion that allows the drive coil windings 140 to be wrapped directly onto the support. The lower support material 146 can still maintain the mechanical load and has a groove 150 to allow access to the drive coil leads.

In FIGS. 17, 18, and 20, the drive coil was inside the washer support material and the sense elements were positioned or scanned on the outside of the fastener. The sense elements can be oriented in different configurations, such as horizontal or vertical, to detect various components of the magnetic field. Similarly, the sense elements can be inside the washer support material and the drive positioned or scanned outside the fastener. The sense elements may also be simply sandwiched between the test material and the fastener head, nut, or other material, as described for sensor arrays in U.S. patent application Ser. Nos. 09/666,879 and 09/666,524, both filed on Sep. 20, 2000, the entire teachings of which are incorporated herein by reference, as long as the conductors for the sense elements are insulated from any metal surfaces Another method for increasing the coupling of the magnetic field from the drive coil into the test material is to use ferrites or other magnetizable materials. For example, the upper support materials (148 in FIG. 17 and FIG. 19, 162 in FIG. 20) could be fabricated from ferrites or a magnetizable composite to help minimize fringing magnetic fields that could couple into the nut or fastener head material. In addition, a cylindrical ring of magnetizable material could be placed around the outside of the support material to help make a magnetic circuit. A coating 164 of magnetizable material could be applied to the fastener shaft or, if hollow fasteners can be used similar to those used for applying sealant into grooves between material layers, the central portion 166 of the fastener could be filled with a magnetizable material. Adding the magnetizable material at different locations in and around the fastener can enhance the penetration of the magnetic field into the test material and enhance sensitivity to the hidden flaws.

The measurement signal can also be improved by repeatedly scanning the sensor over the test material or rotating it around a feature such as a fastener. This permits averaging of the signal and can significantly reduce the background noise level. When repeatedly scanning in this fashion it is important to use a position encoder or ensure that each scan is registered so that the averaging is performed over the same area.

A variety of micro-fabricated sense elements can be used with the drive winding coils mounted around fasteners. For example, linear sense element arrays can be used if the likely crack growth direction is known. Alternatively circular sense element arrays be used, such as the rosettes described in U.S. patent application Ser. Nos. 09/666,879 and 09/666,524, both filed on Sep. 20, 2000. These applications also discuss embedding the sensor arrays in different material layers and beneath the fastener ends. With a given drive location, the sense elements can be located between layers or on the opposite side of a material layer in the same region as the drive. This can provide the desired observability to a feature or material property of interest, such as a buried crack or stress at an interface or stress in a bolt.

As another alternative embodiment, other types of sensing elements, such as Hall effect sensors, flux gate sensors, magnetoresistive sensors, SQUIDS, and giant magnetoresistive (GMR) sensors, can also be used for the measurements. The use of GMR sensors for characterization of materials is described in U.S. patent application Ser. No. 10/045,650, filed Nov. 8, 2001, the entire teachings of which are incorporated herein by reference. While conventional eddy-current sensors are effective at examining near surface properties of materials, but have a limited capability to examine material property variations deep within a material. GMR sensors respond to magnetic fields directly, rather than through an induced response on sensing coils, which permits operation at low frequencies, even DC, and deep penetration of the magnetic fields into the test material. The GMR sensors can be used in place of sensing coils, conventional eddy-current drive coils, or sensor arrays. Thus, the GMR-based sensors can provide a greater depth of sensitivity to hidden features.

While the inventions have been particularly shown and described with reference to preferred embodiments thereof, it will be understood to those skilled in the art that various changes in form and details may be made therein without departing from the spirit and scope of the invention as defined by the appended claims.

REFERENCES INCORPORATED BY
REFERENCE IN THEIR ENTIRETY

Auld, B. A. and Moulder, J. C. (1999), "Review of Advances in Quantitative Eddy-Current Nondestructive Evaluation," Journal of Nondestructive Evaluation, vol. 18, No. 1.

The following references are also incorporated herein by reference in their entirety.

1. Air Force Phase II Proposal, titled "Three Dimensional Magnetic Imaging of Damage in Multiple Layer Aircraft Structures," Topic #AF02-281, dated Feb. 20, 2003.
2. Technical paper titled "*MWM Eddy Current Sensor Array Imaging of Surface and Hidden Corrosion for Improved Fleet Readiness and Cost Avoidance*," presented at U.S. Army Corrosion Conference, Clearwater Beach; Fla., Feb. 11-13, 2003.
3. Technical paper titled "*MWM Eddy Current Sensor Array Characterization of Aging Structures Including Hidden Damage Imaging*," presented to the Aerospace Committee, NACE Conference, San Diego; Calif., Mar. 17-19, 2003.

What is claimed is:

1. A method for monitoring damage at a fastener comprising:
   mounting a drive coil having at least two conducting wire windings with a support material shaped in the form of a washer, the windings being wrapped around a sleeve along a length of the fastener;
   placing the washer on a test substrate under the fastener;
   placing at least one microfabricated sense element proximate to the drive coil; and
   measuring a response from each sense element as a magnetic field is imposed in the test substrate by an electric current driven through the drive coil.

2. The method as claimed in claim 1 wherein the at least one sense element is an inductive coil.

3. The method as claimed in claim 1 wherein the at least one sense element is a giant magnetoresistive sensor.

4. The method as claimed in claim 1 wherein the at least one sense element responds to a different component of the magnetic field than another sense element.

5. The method as claimed in claim 1 wherein the at least one sense element is at a different radial distance from the drive coil than another sense element.

6. The method as claimed in claim 1 wherein the support material has a lower electrical conductivity than the electrical conductivity of the test substrate.

7. The method as claimed in claim 6 wherein the support material is a composite.

8. The method as claimed in claim 1 wherein the support material is split to reduce induced eddy currents in the support material.

9. The method as claimed in claim 1 wherein the drive coil is enclosed by the support material.

10. The method as claimed in claim 1 wherein the support material includes a magnetizable material.

11. The method as claimed in claim 10 wherein the magnetizable material is a ferrite.

12. The method as claimed in claim 1 wherein the shaft of the fastener is coated with a magnetizable material.

13. The method as claimed in claim 1 wherein the fastener has a hollow shaft filled with a magnetizable material.

14. The method as claimed in claim 1 further comprising scanning a sense element around the fastener.

15. A method for monitoring damage at a fastener comprising:
    placing a drive coil having at least one conducting wire winding wrapped around a sleeve along a length of the fastener;
    mounting at least one microfabricated sense element to a test substrate under the fastener; and
    measuring a response from each sense element as a magnetic field is imposed in the test substrate by an electric current driven through the drive coil.

16. The method as claimed in claim 15 wherein the at least one sense element is an inductive coil.

17. The method as claimed in claim 15 wherein the at least one sense element is at a different radial distance from the drive coil than another sense element.

18. The method as claimed in claim 15 wherein the at least one sense element is mounted into a support material formed into a washer.

19. The method as claimed in claim 15 wherein the support material has a lower electrical conductivity than the electrical conductivity of the test substrate.

20. The method as claimed in claim 19 wherein the support material is a composite.

21. The method as claimed in claim 18 wherein the support material is split to reduce induced eddy currents in the support material.

22. The method as claimed in claim 18 wherein the support material includes a ferrite.

23. The method as claimed in claim 15 wherein the shaft of the fastener is coated with a magnetizable material.

24. The method as claimed in claim 15 wherein the fastener has a hollow shaft filled with a magnetizable material.

25. The method as claimed in claim 15 wherein the fastener further comprises a nut and the nut has an electrical conductivity lower than the electrical conductivity of the test substrate.

26. The method as claimed in claim 15 further comprising:
    scanning the drive coil around the fastener.

27. The method as claimed in claim 15 further comprising:
    measuring the response at multiple proximities to the test material surface.

28. A test circuit comprising:
    at least one conducting winding wrapped around a sleeve along a length of a fastener; and
    at least one microfabricated sense element mounted on a test substrate under the fastener, the at least one sense element being configured to provide a response as a magnetic field is imposed in the test substrate by an electric current driven through the at least on conducting winding.

29. The test circuit as claimed in claim 28 wherein the at least one sense element is mounted into a support material formed into a washer.

30. The test circuit as claimed in claim 28 wherein the support material is split to reduce induced eddy currents in the support material.

* * * * *